(12) United States Patent
Van Slyke

(10) Patent No.: US 8,222,018 B2
(45) Date of Patent: Jul. 17, 2012

(54) GORDONIA SIHWENSIS STRAIN AND USES THEREOF

(75) Inventor: Donald C. Van Slyke, Richmond, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 604 days.

(21) Appl. No.: 12/338,581

(22) Filed: Dec. 18, 2008

(65) Prior Publication Data

US 2010/0159568 A1 Jun. 24, 2010

(51) Int. Cl.
*C12N 1/20* (2006.01)
(52) U.S. Cl. .................... 435/252.1; 435/262.5
(58) Field of Classification Search ............ None
See application file for complete search history.

(56) References Cited

U.S. PATENT DOCUMENTS

| 2003/0036187 A1 | 2/2003 | Fujita |
| 2005/0077249 A1 | 4/2005 | Kerfoot |
| 2008/0020947 A1 | 1/2008 | Park et al. |

FOREIGN PATENT DOCUMENTS

WO WO 2008/037718 4/2008

OTHER PUBLICATIONS

Kummer et al.., (1999), International Journal of Systematic Bacteriology vol. 49, pp. 1513-1522.*
Arenskötter et al., Biology of the metabolically diverse genus *Gordonia*. Appl Environ Microbiol. Jun. 2004;70(6):3195-3204.
Franzetti et al., "Surface-active compounds and their role in the access to hydrocarbons in *Gordonia* strains." FEMS Microbiol Ecol. Feb. 2008;63(2):238-248.
International Search Report of Patent Application No. PCT/US2009/066799, filed Dec. 4, 2009 by Chevron U.S.A. Inc. et al.
Kim et al., "*Gordonia sihwensis* sp. nov., a novel nitrate-reducing bacterium isolated from a wastewater-treatment bioreactor." Int J Syst Evol Microbiol. Sep. 2003;53(Pt 5):1427-1433.
Lin et al., "Exopolysaccharides produced by *Gordonia alkanivorans* enhance bacterial degradation activity for diesel." Biotechnol. Lett. 2008, 30:1201-1206.
Rosenberg et al., "Bioemulsans: surface-active polysaccharide-containing complexes". Biopolymers 2002, 5:91-111.
Saeki et al., "Oil spill remediation by using the remediation agent JE1058BS that contains a biosurfactant produced by *Gordonia* sp. strain JE-1058." Bioresour Technol. Jan. 2009;100(2):572-7. Epub Aug. 8, 2008.
Shen and Young, "Rapid detection and identification of the metabolically diverse genus *Gordonia* by 16S rRNA-gene-targeted genus-specific primers." FEMS Microbiol Lett, Sep. 15, 2005;250(2):221-227.
Shen et al., "Molecular detection and phylogenetic characterization of *Gordonia* species in heavily oil-contaminated soils," Res. Microbiol, Sep.-Oct. 2008:159(7-8):522-9, Epub Aug. 3, 2008.
SRS Search result of *Gordonia sihwensis* Strain from CABRI and DDBJ in Apr. 2008.
Bouchez-Naïtali et al., "Diversity of bacterial strains degrading hexadecane in relation to the mode of substrate uptake," *J. Appl. Microbiol.* 86: 421-428 (1999).
Schaeffer et al., "Microbial growth on hydrocarbons: terminal branching inhibits biodegradation," *Appl. Environ. Microbiol.* 38: 742-746 (1979).

* cited by examiner

*Primary Examiner* — Irene Marx
(74) *Attorney, Agent, or Firm* — Brian R. Dorn; Barnes & Thornburg LLP

(57) ABSTRACT

Described herein is a strain of *Gordonia sihwensis*. The *Gordonia sihwensis* strain described herein may be used to sequester and/or biodegrade hydrocarbons. In particular, the *Gordonia sihwensis* strain described herein may be used in the remediation of drill cuttings coated with drilling fluid.

5 Claims, 8 Drawing Sheets

EcoRI

Figure 2:
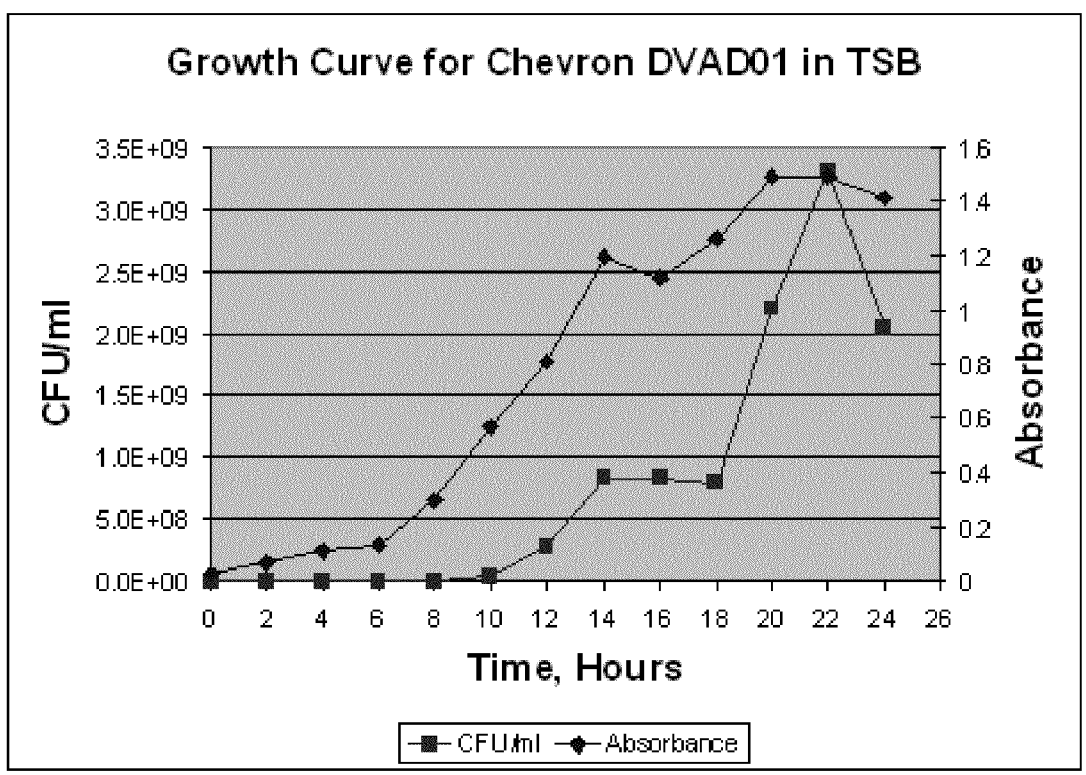
Figure 3:
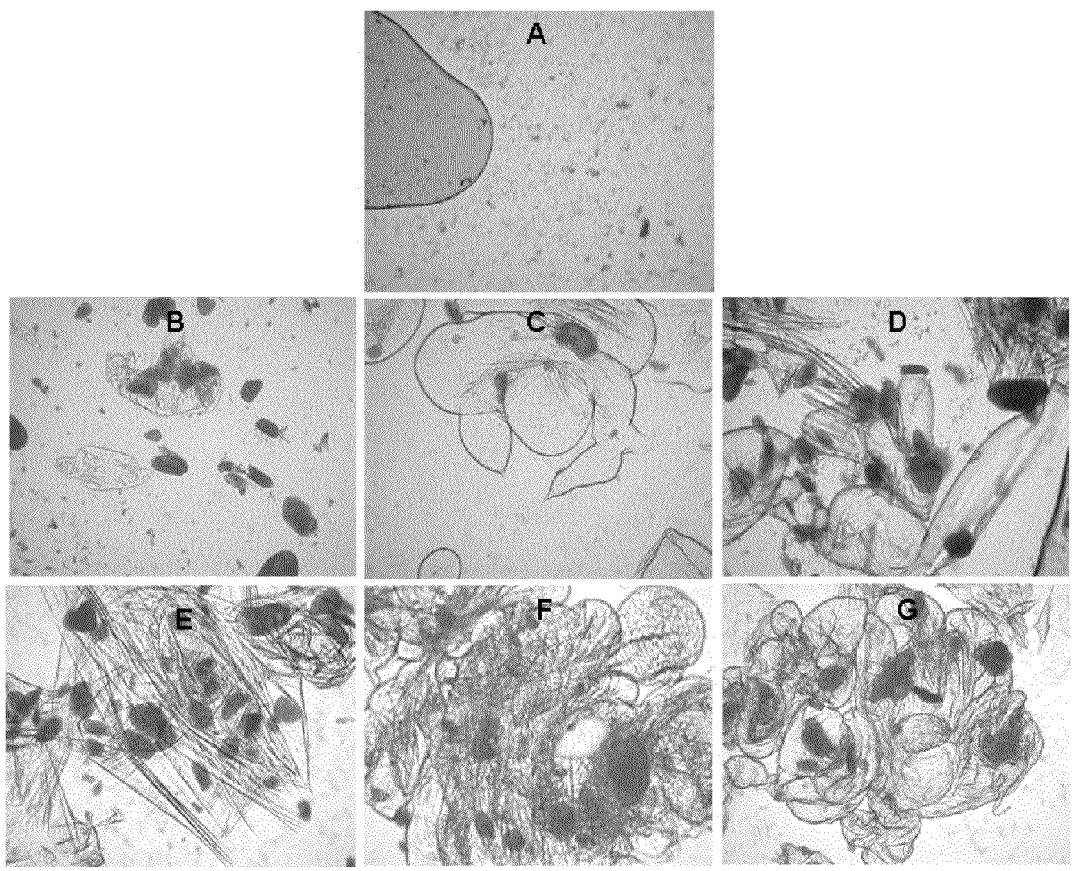

| How Assigned | Number | Label | RiboGroup | RiboPrint™ Pattern |
|---|---|---|---|---|
| HLA1 | 462-507-S-6 | R1842-1114070-NC-DMI-B | HLA1 462-507-S-6 | |

PvuII

| How Assigned | Number | Label | RiboGroup | RiboPrint™ Pattern |
|---|---|---|---|---|
| HLA1 | 462-508-S-6 | R1842-1114070-NC-DMI-B | HLA1 462-508-S-6 | |

Fig. 1

*GORDONIA SIHWENSIS* STRAIN AND USES THEREOF

1. FIELD

Described herein is a strain of *Gordonia sihwensis*. The *Gordonia sihwensis* strain described herein may be used to sequester and/or biodegrade hydrocarbons. In particular, the *Gordonia sihwensis* strain described herein may be used in the remediation of drill cuttings coated with drilling fluid.

2. BACKGROUND

Environmental pollution with hydrocarbons poses a major concern. Crude oil is a major sea pollutant, and petroleum products, such as gasoline and diesel fuel and fuel oils, are the most frequent organic pollutants of soils and ground waters. In the drilling of oil and gas wells, oil-based drilling fluid is required in most of the challenging drilling situations, and the spent oil-coated drill cuttings cannot typically be discharged from the drilling rig for environmental reasons. A rapid biodegradation of oil on such cuttings could render oil-based drilling fluids as environmentally acceptable as water-based drilling fluids.

There are two primary types of drilling fluids: (i) water based drilling fluids (WBF); and (ii) non-aqueous drilling fluids (NADFs). WBFs comprise water mixed with bentonite clay and barite to control mud density and thus, hydrostatic head. Other substances can be added to affect one or more desired drilling properties. NADFs are either based on mineral oil, diesel, or synthetic base fluid. NADFs are typically water in oil (invert) emulsions. In rare cases, such as with coring fluids, 100% oil-based drilling fluids have been used. NADFs are generally preferred over water-based fluids for their ability to provide superior borehole stability, lubricity, rate of penetration, stuck pipe prevention, chemical stability, and corrosion protection.

In contrast to WBFs and WBF-coated cuttings that can typically be discharged into the environment, in many areas regulatory standards do not allow the discharge of NADFs, or drill cuttings coated with NADF into the environment. If NADF-coated cuttings are not permitted to be discharged into the environment, then the cuttings must either be reinjected, hauled to shore, thermally treated to remove base fluid, or land farmed. In some regions, drill cuttings coated with NADF can be discharged into the environment if the base fluid and/or whole mud is approved for discharge. In many cases, cutting dryers are used to remove most of the NADF from the cuttings prior to discharge.

The inability to discharge technically superior NADF and NADF cuttings into the environment presents a huge problem for the oil and gas industry. In many drilling situations, NADFs must be used in order to economically drill the well. This is particularly true with high angle wells, horizontal wells, high pressure high temperature wells, deepwater wells, slimhole wells, and wells drilled into water-sensitive formations.

Many technologies have been developed to deal with the problem of NADF disposal. However, each of these systems has limitations. Cuttings drying is expensive and can only achieve a reduction in oil on cuttings down to 3-4% by weight. The injection of cuttings containing NADF has limitation due to the equipment requirement to capture the cuttings, slurrify them and pump them down an annulus, the lack of available annuli, and the poor understanding of the fracture process involved. Hauling of cuttings containing NADF is expensive and results in non-water quality environmental impacts, including air pollution from transportation, energy use during transportation, and disposal site factors. Landfarming of cuttings requires large areas of land, is a slow process and creates environmental concerns due to the potential for leaching and runoff. Thermal processing of cuttings is expensive, requires a large footprint, and creates safety concerns due to the high temperatures involved.

Thus, methodologies that make the drill cuttings more environmentally acceptable would be valuable.

3. SUMMARY

Described herein is a strain of *Gordonia sihwensis* which has been deposited with the ATCC and assigned ATCC Accession No. PTA-9635. In a specific embodiment, provided herein is a biologically pure culture of the *Gordonia sihwensis* strain described herein. Any technique known to one of skill in the art may be used to obtain a biologically pure culture of bacteria. Generally, a bacterial sample is streaked onto a solid agar-containing medium so as to separate the bacteria present in the sample into individual cells that grow as individual colonies. In one embodiment, a culture of an individual colony from such solid-agar containing medium is considered a biologically pure culture.

In one embodiment, provided herein is a suitable container or vessel comprising the *Gordonia sihwensis* strain described herein. In specific embodiments, the container or vessel comprises a biologically pure culture of the *Gordonia sihwensis* strain described herein. In other embodiments, the container or vessel comprises a mixture of the *Gordonia sihwensis* strain described herein and one or more other microorganisms (e.g., bacterial species). In a specific embodiment, the container or vessel comprises a biologically pure culture of the *Gordonia sihwensis* strain described herein and a biologically pure culture of one or more other microorganisms (e.g., bacterial species). In certain embodiments, the one or more other microorganisms are capable of sequestering and/or biodegrading hydrocarbons. In certain embodiments, the container or vessel comprises culture medium. In some embodiments, the container or vessel comprises one or more types of hydrocarbons.

In another embodiment, described herein is a composition comprising the *Gordonia sihwensis* strain described herein. In specific embodiments, the composition comprises a biologically pure culture of the *Gordonia sihwensis* strain described herein. In other embodiments, the composition comprises a mixture of the *Gordonia sihwensis* strain described herein and one or more other microorganisms. In a specific embodiment, the composition comprises a biologically pure culture of the *Gordonia sihwensis* strain described herein and a biologically pure culture of one or more other microorganisms (e.g., bacterial species). In certain embodiments, the one or more other microorganisms are capable of sequestering and/or biodegrading hydrocarbons. In certain embodiments, the composition comprises culture medium. In some embodiments, the composition comprises one or more types of hydrocarbons.

In another embodiment, described herein is a composition comprising media conditioned by the *Gordonia sihwensis* strain described herein. In some embodiments, the conditioned media may be used to sequester hydrocarbons. In one embodiment, a method for sequestering hydrocarbons comprises contacting a composition comprising one or more hydrocarbons with media conditioned by the *Gordonia sihwensis* strain described herein under conditions which permit the sequestration of the hydrocarbons. In a specific embodiment, the conditioned media is obtained from a culture (e.g., a biologically pure culture) of the *Gordonia sihwensis* strain described herein while the bacteria is in log phase or stationary phase.

In one aspect, the *Gordonia sihwensis* strain described herein may be used to sequester hydrocarbons. In one embodiment, in the presence of hydrocarbons, the *Gordonia sihwensis* strain described herein forms a sac-like structure that surrounds the hydrocarbons. In another embodiment, hydrocarbons are incorporated into a sac-like structure produced by the *Gordonia sihwensis* strain described herein. In another embodiment, the *Gordonia sihwensis* strain described herein forms a sac-like structure around hydrocarbons and/or incorporates hydrocarbons into a sac-like structure. In one embodiment, a method for sequestering hydrocarbons comprises contacting a composition comprising one or more hydrocarbons with the *Gordonia sihwensis* strain described herein under conditions which permit the sequestration of the hydrocarbons. In another embodiment, a method for sequestering hydrocarbons comprises contacting a first composition comprising one or more hydrocarbons with a second composition comprising the *Gordonia sihwensis* strain described herein under conditions which permit the sequestration of the hydrocarbons. In a specific embodiment, the second composition is a culture (e.g., a biologically pure culture) of the *Gordonia sihwensis* strain described herein.

In another aspect, the *Gordonia sihwensis* strain described herein may be used to biodegrade hydrocarbons. The *Gordonia sihwensis* strain described herein may completely biodegrade hydrocarbons to carbon dioxide or alter the structure of hydrocarbons to produce an intermediate metabolite or biochemical compound. In one embodiment, the *Gordonia sihwensis* strain described herein transforms an original hydrocarbon structure to carbon dioxide. In another embodiment, the *Gordonia sihwensis* strain described herein alters an original hydrocarbon structure to form an intermediate metabolite or biochemical compound, such as, e.g., a fatty acid or alcohol. In a specific embodiment, a method for biodegrading hydrocarbons comprises contacting a composition comprising one or more hydrocarbons with the *Gordonia sihwensis* strain described herein under conditions which permit the biodegradation of the hydrocarbons. In another embodiment, a method for biodegrading hydrocarbons comprises contacting a first composition comprising one or more hydrocarbons with a second composition comprising the *Gordonia sihwensis* strain described herein under conditions which permit the biodegradation of the hydrocarbons. In a specific embodiment, the second composition is a culture (e.g., a biologically pure culture) of the *Gordonia sihwensis* strain described herein.

In another aspect, the *Gordonia sihwensis* strain described herein is used to sequester and biodegrade hydrocarbons. In a specific embodiment, a method for sequestering and biodegrading hydrocarbons comprises contacting a composition comprising one or more hydrocarbons with the *Gordonia sihwensis* strain described herein under conditions which permit the sequestration and biodegradation of the hydrocarbons. In another embodiment, a method for sequestering and biodegrading hydrocarbons comprises contacting a first composition comprising one or more hydrocarbons with a second composition comprising the *Gordonia sihwensis* strain described herein under conditions which permit the biodegradation of the hydrocarbons. In a specific embodiment, the second composition is a culture (e.g., a biologically pure culture) of the *Gordonia sihwensis* strain described herein. Non-limiting examples of conditions which permit either the sequestration or biodegradation of hydrocarbons, or both are described herein.

In a specific aspect, the *Gordonia sihwensis* strain described herein may be used in the remediation of drill cuttings coated with drilling fluid. In another aspect, the *Gordonia sihwensis* strain described herein may be used in the remediation of soil or sludges contaminated with diesel, gasoline, crude oil, or other oil contaminants. In another aspect, the *Gordonia sihwensis* strain described herein may be used in the clean-up of oil, gasoline or diesel spills. In yet another aspect, the *Gordonia sihwensis* strain described herein may be used to remove oil, gasoline or diesel from produced water or any quantity water that has been contaminated with oil, gasoline or diesel.

4. BRIEF DESCRIPTION OF THE FIGURES

FIG. 1. Ribotype pattern for the *Gordonia sihwensis* strain described herein.

FIG. 2. A growth curve for the *Gordonia sihwensis* strain described herein grown in tryptic soy broth fermentation media.

FIGS. 3A-3G. Microscope photos of aliquots of bacteria taken at 40× magnification at approximately 0 minutes (FIG. 3A), 2 minutes (FIG. 3B), 5 minutes (FIG. 3C), 13 minutes (FIG. 3D), 30 minutes (FIG. 3E), 1 hour (FIG. 3F) and 2 hours (FIG. 3G) after the addition of 2% Estegreen and oil soluble dye to flasks containing the *Gordonia sihwensis* strain described herein grown in TSB.

Figure 4:
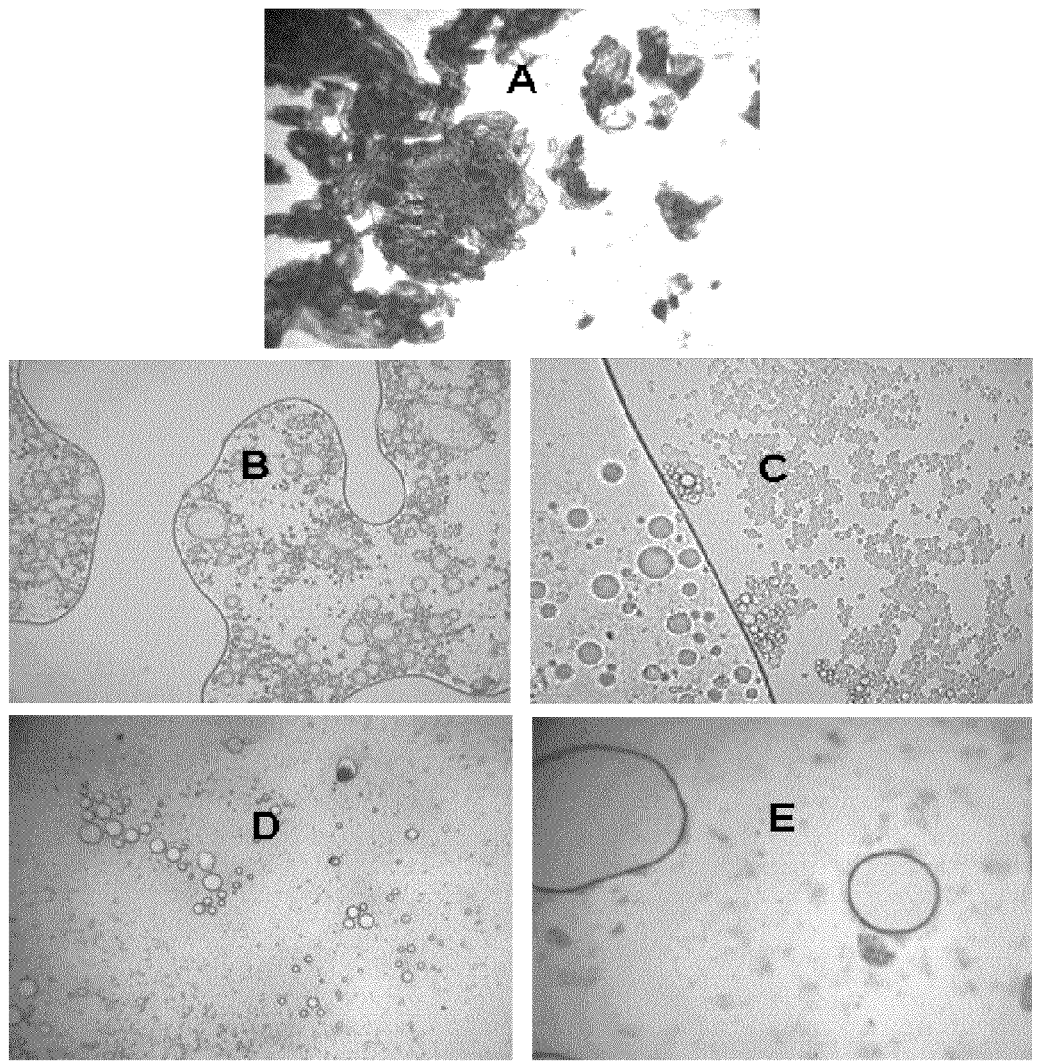

FIGS. 4A-4E. Microscope photos of aliquots of bacteria taken at 40× magnification from flasks with or without different types of surfactant. FIG. 4A. Surfactant-free after 15 minutes; FIG. 4B. 0.02% Triton® X-100 after 15 minutes; FIG. 4C. 0.02% Triton® X-100 after 2 hours; FIG. 4D. 0.12% Centrolex lecithin after 15 minutes; and FIG. 4E. 0.6% rhamnolipid biosurfactant after 15 minutes.

Figure 5:
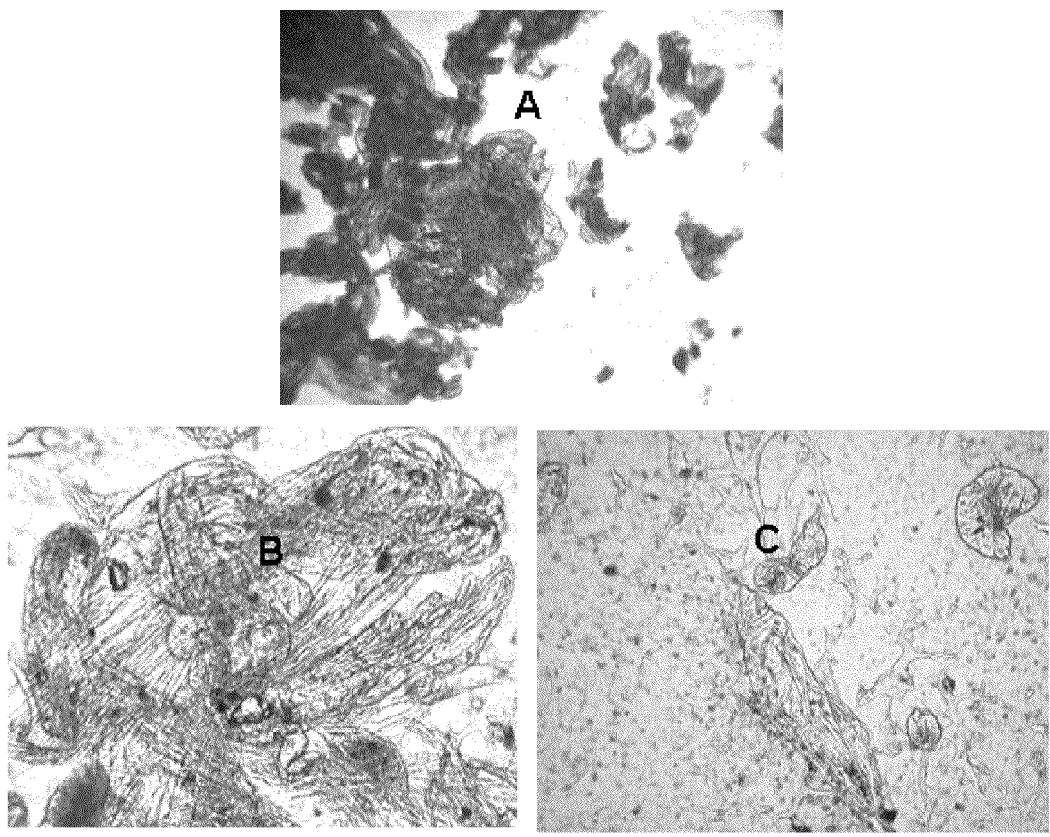

FIGS. 5A-5C. Microscope photos of aliquots of bacteria taken at 40× magnification from flasks containing 2% Estegreen oil with or without different amounts of drill solids. FIG. 5A. no drill solids; FIG. 5B. 5 grams of drill solids; and FIG. 5C. 10 grams of drill solids.

Figure 6:
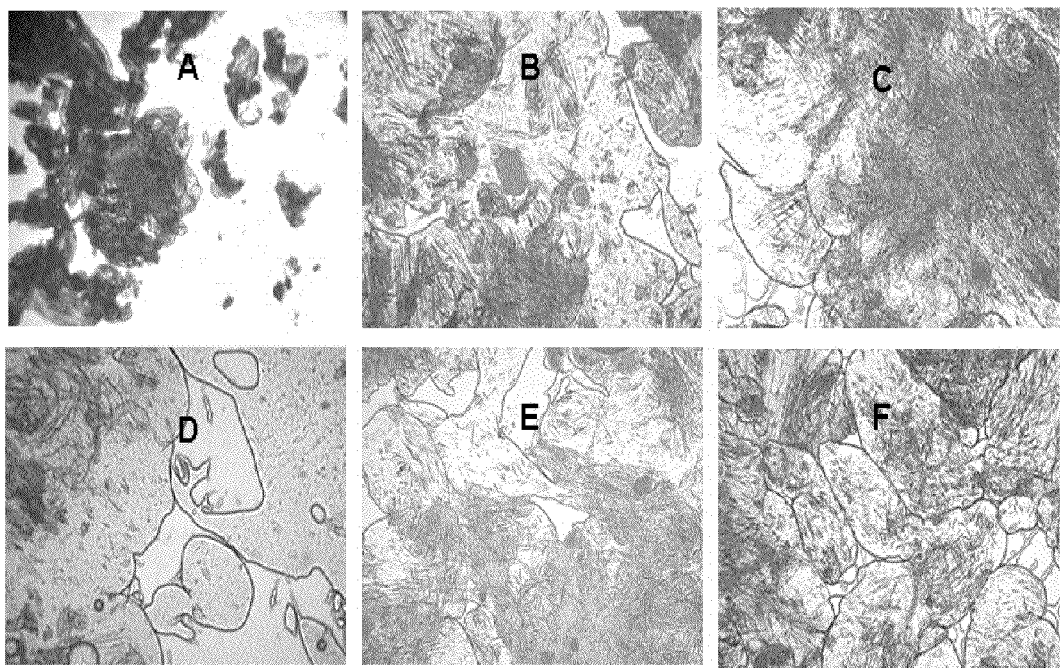

FIGS. 6A-6F. Microscope photos of aliquots of bacteria taken at 40× magnification from flasks incubated for 15 minutes with or without different types of oil. FIG. 6A. Estegreen; FIG. 6B. diesel oil; FIG. 6C. Puredrill IA35LV; FIG. 6D. Ametek white oil; FIG. 6E. kerosene; and FIG. 6F. HDF-2000.

Figure 7:
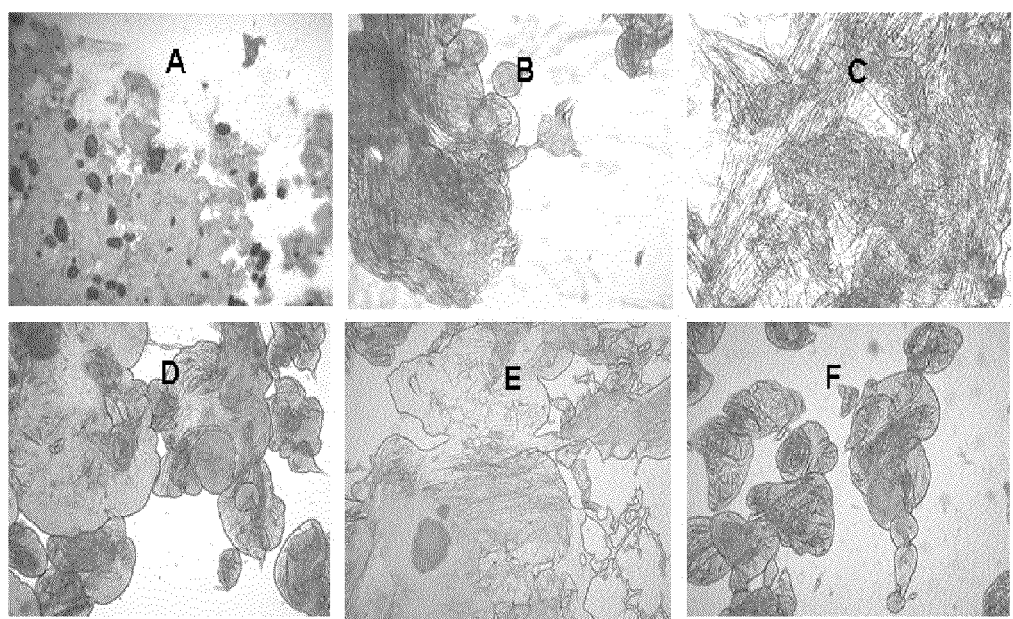

FIGS. 7A-7F. Microscope photos of aliquots of bacteria taken at 40× magnification from flasks incubated for 1 hour with or without different types of oil. FIG. 7A. Estegreen; FIG. 7B. diesel oil; FIG. 7C. Puredrill IA35LV; FIG. 7D. Ametek white oil; FIG. 7E. kerosene; and FIG. 7F. HDF-2000.

Figure 8:
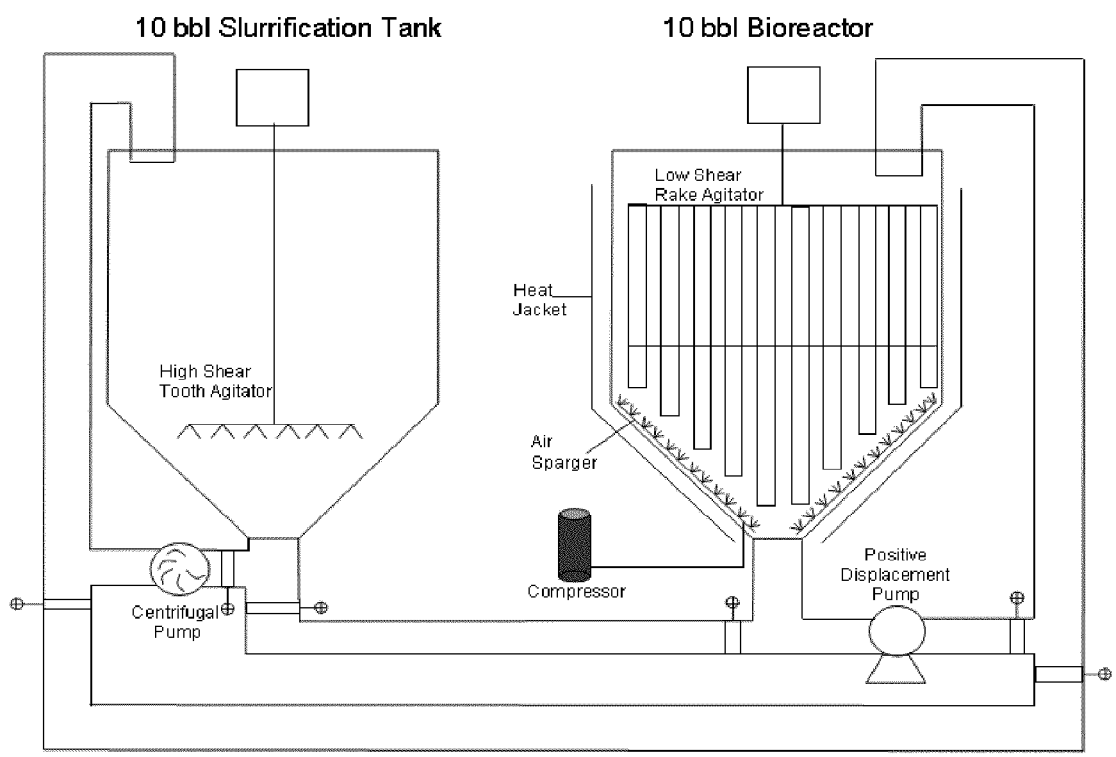

FIG. 8. Schematic of bioreactor and slurrification tank.

Figure 9:
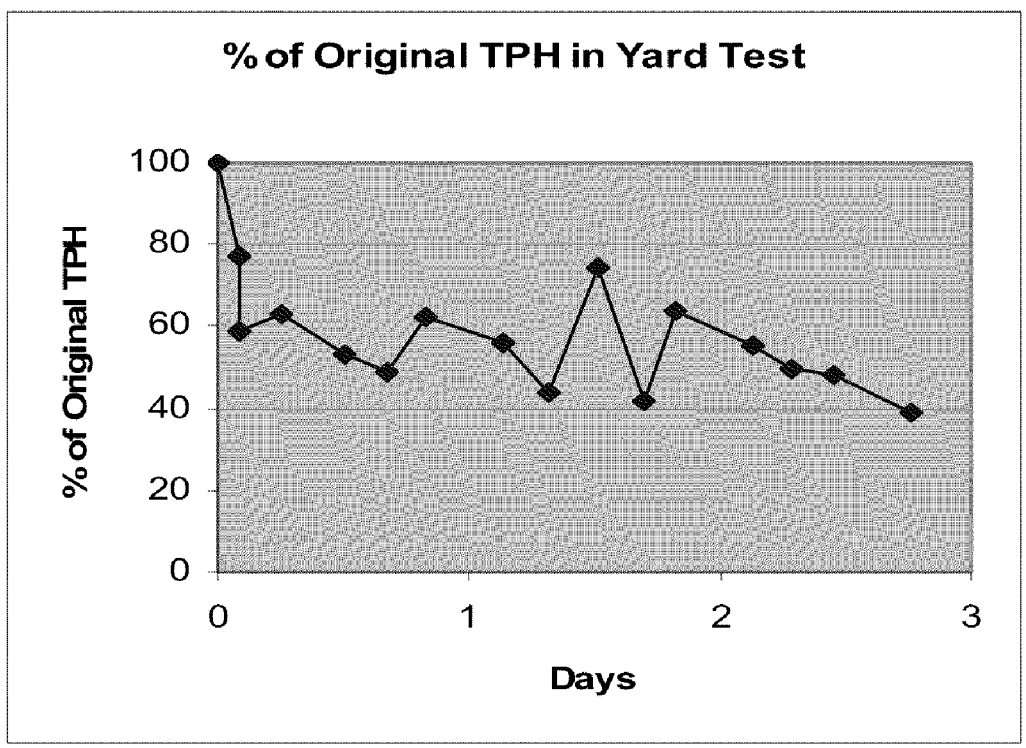

FIG. 9. Percentage of original total petroleum hydrocarbons in the bioreactor.

5. DETAILED DESCRIPTION

Described herein is a gram-positive, rod-shaped bacterial organism that has been classified as a strain from the species *Gordonia sihwensis*. *Gordonia sihwensis* strain Chevron DVAD01 was deposited with the American Type Culture Collection (ATCC), located at 10801 University Boulevard, Manassas, Va. 20110-2209 on Nov. 21, 2008, and assigned ATCC Accession No. PTA-9635. This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Chevron and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. 122 and the Commissioner's rules pursuant thereto (including 37 C.F.R. 1.14 with particular reference to 886 OG 638). Thereby, the deposited biological materials will be irrevocably and without restriction or condition released to the public upon the issuance of a patent.

5.1 Culture Conditions for Proliferation of the Bacteria

The *Gordonia sihwensis* strain described herein may be grown under aerobic conditions. The *Gordonia sihwensis* strain described herein may be grown in a vessel or container commonly used to culture microorganisms, such as flasks, plates, bioreactors, including by way of example and not limitation, stirred-tank or airlift bioreactors (suspension reactors). In certain embodiments, the *Gordonia sihwensis* strain described herein is grown in a 5 mL, 10 mL, 20 mL, 50 mL, 100 mL, 200 mL, 500 mL. 1 L, 2 L, 3 L, 4 L, 5 L, 10 L, 100 L, 500 L, 1000 L, 5000 L, 10000 L or 15000 L vessel or container commonly used to culture microorganisms. The *Gordonia sihwensis* strain described herein may be grown in any vessel or container suitable for laboratory use or commercial use of the bacteria. In a specific embodiment, a biologically pure culture of the *Gordonia sihwensis* strain described herein is grown in any vessel or container suitable for laboratory use or commercial use of the bacteria.

Any device used in the art for maintaining culture conditions (such as temperature, pH, oxygenation, etc.) may be used as part of, or in conjunction with, a vessel or container commonly used to culture microorganisms. In a specific embodiment, the temperature of the culture is maintained at approximately 25° C. to approximately 45° C., approximately 30° C. to approximately 45° C., approximately 35° C. to approximately 45° C., approximately 35° C. to approximately 40° C. In another embodiment, the temperature of the culture is maintained at approximately 30° C., 31° C., 32° C., 33° C., 34° C., 35° C., 36° C., 37° C., 38° C., 39° C., 40° C., 41° C., 42° C., 43° C., 44° C. or 45° C. In certain embodiments, the pH of the culture medium is monitored during the culture process so that the pH remains at approximately pH 6.0 to approximately pH 8.0, approximately pH 6.8 to approximately pH 7.6, approximately pH 7.0 to approximately pH 7.6, approximately pH 7.0 to approximately pH 7.4, approximately pH 7.0 to approximately pH 7.2 or approximately pH 7.0. In another embodiment, the bacterial culture is shaken at approximately 10 rpm to approximately 25 rpm, approximately 25 to approximately 50 rpm, approximately 25 to approximately 75 rpm, approximately 50 to approximately 100 rpm, or approximately 75 rpm to approximately 100 rpm. In other embodiments, the bacterial culture is shaken at approximately 100 rpm to approximately 400 rpm or approximately 150 rpm to approximately 300 rpm in the vessel or container. Sufficient aeration is provided to the bacterial culture to maintain a sufficient concentration of dissolved oxygen. In a specific embodiment, sufficient aeration is provided to maintain a dissolved oxygen concentration of approximately 0.5 mg/L to approximately 25 mg/L, approximately 1 mg/L to approximately 25 mg/L, approximately 1 mg/L to approximately 20 mg/L, approximately 1 mg/L to approximately 15 mg/L, approximately 1 mg/L to approximately 10 mg/L, approximately 1 mg/L to approximately 5 mg/L, or approximately 5 mg/L to approximately 20 mg/L.

As used herein, the terms "about" and "approximately", unless otherwise indicated, refer to a value that is no more than 20% above or below the value being modified by the term.

Any microbial culture medium known in the art may be suitable to grow the *Gordonia sihwensis* strain described herein. The suitability of a particular microbial culture medium can be determined using methods known in the art or described herein. For example, the suitability of a particular medium may be determined by assessing the proliferation of the bacteria or the ability of the bacteria to form sac-like structures. In one embodiment, the culture media is nutrient broth. In another embodiment, the culture media is tryptic soy broth (TSB). In another embodiment, the culture media is 50/50 TSB/enhanced Inakollu mineral media. In another embodiment, the culture media is brain heart infusion (BHI) broth. In certain embodiments, the *Gordonia sihwensis* strain described herein is grown in medium in which the sole carbon source is a hydrocarbon. In some embodiments, the *Gordonia sihwensis* strain described herein is grown in medium in which the sole carbon source is a mixture of two or more types of hydrocarbons.

Any technique known in the art may be used to inoculate a suitable microbial culture medium. The amount bacteria in the inoculum will vary depending upon a number of factors, including, e.g., the size of the vessel or container and the volume of the culture medium. In a specific embodiment, an inoculum of approximately 5,000 colony forming units (CFU) to approximately 50,000,000 CFU, approximately 5,000 CFU to approximately 40,000,000 CFU, approximately 5,000 CFU to approximately 30,000,000 CFU, approximately 5,000 CFU to approximately 25,000,000 CFU, approximately 5,000 CFU to approximately 15,000,000 CFU or approximately 5,000 CFU to approximately 10,000,000 CFU is used to inoculate a suitable microbial cell culture medium. In another embodiment, an inoculum of approximately 10,000 CFU to approximately 50,000,000 CFU, approximately 10,000 CFU to approximately 40,000,000 CFU, approximately 10,000 CFU to approximately 30,000,000 CFU, approximately 10,000 CFU to approximately 25,000,000 CFU, approximately 10,000 CFU to approximately 15,000,000 CFU or approximately 10,000 CFU to approximately 10,000,000 CFU is used to inoculate a suitable microbial cell culture medium. In another embodiment, an inoculum of approximately 25,000 CFU to approximately 50,000,000 CFU, approximately 25,000 CFU to approximately 40,000,000 CFU, approximately 25,000 CFU to approximately 30,000,000 CFU, approximately 25,000 CFU to approximately 25,000,000 CFU, approximately 25,000 CFU to approximately 15,000,000 CFU or approximately 25,000 CFU to approximately 10,000,000 CFU is used to inoculate a suitable microbial cell culture medium. In yet another embodiment, an inoculum of approximately 10,000 CFU to approximately 5,000,000 CFU, approximately 10,000 CFU to approximately 2,000,000 CFU, approximately 10,000 CFU to approximately 1,000,000 CFU, approximately 10,000 CFU to approximately 750,000 CFU, approximately 10,000 CFU to approximately 500,000 CFU or approximately 10,000 CFU to approximately 250,000 CFU is used to inoculate a suitable microbial cell culture medium.

5.2 Sequestration and Biodegradation

In one aspect, a composition comprising media conditioned by the *Gordonia sihwensis* strain described herein may be used to sequester hydrocarbons. In one embodiment, a method for sequestering hydrocarbons comprises contacting a composition comprising one or more hydrocarbons with media conditioned by the *Gordonia sihwensis* strain described herein under conditions which permit the sequestration of the hydrocarbons. In a specific embodiment, the conditioned media is obtained from a culture (e.g., a biologically pure culture) of the *Gordonia sihwensis* strain described herein while the bacteria is in log phase or stationary phase.

In another aspect, the *Gordonia sihwensis* strain described herein is capable of sequestering hydrocarbons. In one embodiment, the *Gordonia sihwensis* strain described herein forms a sac-like structure around hydrocarbons, such as the sac-like structures shown in FIGS. 3-7. In another embodiment, hydrocarbons are incorporated into a sac-like structure produced by the *Gordonia sihwensis* strain described herein. In a specific embodiment, in microbial culture medium, the *Gordonia sihwensis* strain described herein forms a sac-like structure around hydrocarbons and/or incorporates hydrocarbons into a sac-like structure.

In one embodiment, a method for sequestering hydrocarbons comprises contacting a hydrocarbon composition (see Section 5.3 below for a description of hydrocarbon compositions) with a culture or an inoculum of the *Gordonia sihwensis* strain described herein under conditions which permit the sequestration of the hydrocarbon(s) present in the composition. In another embodiment, a method for sequestering hydrocarbons comprises contacting a hydrocarbon composition with a composition comprising the *Gordonia sihwensis* strain described herein under conditions which permit the sequestration of the hydrocarbon(s) present in the composition. In a specific embodiment, the bacterial composition is a biologically pure culture of the *Gordonia sihwensis* strain described herein. Non-limiting examples of conditions which permit the sequestration of a hydrocarbon(s) are described below.

In one embodiment, the capability of the *Gordonia sihwensis* strain described herein or medium conditioned by the bacteria to sequester hydrocarbons is assessed by a technique known to one of skill in the art. In some embodiments, the technique used is one that is used to assess the presence of a biosurfactant. In a specific embodiment, the capability of the *Gordonia sihwensis* strain described herein or medium conditioned by the bacteria to sequester hydrocarbons is assessed using one of the assays described in the example section herein.

Without being bound by any theory, the sequestration of hydrocarbons by the *Gordonia sihwensis* strain described herein into sac-like structures may be advantageous because: (1) inefficient contact between bacteria and hydrocarbons has been a long-standing limitation in hydrocarbon biodegradation, and (2) the sac-like structures may remove hydrocarbons from the environment for a period of time.

In certain embodiments, the sequestration of hydrocarbons by the *Gordonia sihwensis* strain described herein is in rich media (i.e., media that contains a carbon source other than the hydrocarbons being sequestered or biodegraded such as meat extract or peptide extract). Without being bound by any theory, the sequestration of hydrocarbons by the *Gordonia sihwensis* strain described herein in rich media may be advantageous because the bacteria can be grown to a high population density in a relatively short period of time. In some embodiments, the sequestration of hydrocarbons by the *Gordonia sihwensis* strain described herein is in lean media (e.g., mineral media such as Inakollu media or enhanced Inakollu media). Without being bound by theory, the sequestration of hydrocarbons by the *Gordonia sihwensis* strain described herein in lean media (e.g., mineral media such as Inakollu media or enhanced Inakollu media) may not be as advantageous as rich media because there may be a longer lag period for growth in lean media.

In another aspect, the *Gordonia sihwensis* strain described herein biodegrades hydrocarbons. In a specific embodiment, in microbial culture medium, the *Gordonia sihwensis* strain described herein biodegrades hydrocarbons when hydrocarbons are added to the media. The *Gordonia sihwensis* strain described herein may completely biodegrade hydrocarbons to carbon dioxide or alter the structure of hydrocarbons to produce an intermediate metabolite or biochemical compound. In one embodiment, the *Gordonia sihwensis* strain described herein transforms an original hydrocarbon structure to carbon dioxide. In another embodiment, the *Gordonia sihwensis* strain described herein alters an original hydrocarbon structure to form an intermediate metabolite or biochemical compound, such as, e.g., a fatty acid or alcohol.

In certain embodiments, the biodegradation of hydrocarbons by the *Gordonia sihwensis* strain described herein occurs in rich media (i.e., media that contains a carbon source other than the hydrocarbons being sequestered or biodegraded such as meat extract or peptide extract). In some embodiments, the biodegradation of hydrocarbons by the *Gordonia sihwensis* strain described herein occurs in lean media (e.g., mineral media such as Inakollu media or enhanced Inakollu media).

In a specific embodiment, a method for biodegrading hydrocarbons comprises contacting a hydrocarbon composition with a culture or an inoculum of the *Gordonia sihwensis* strain described herein under conditions which permit the biodegradation of the hydrocarbon(s) present in the composition. In another embodiment, a method for biodegrading hydrocarbons comprises contacting a hydrocarbon composition with a composition comprising the *Gordonia sihwensis* strain described herein under conditions which permit the sequestration of the hydrocarbon(s) present in the composition. In a specific embodiment, the bacterial composition is a biologically pure culture of the *Gordonia sihwensis* strain described herein. Non-limiting examples of conditions which permit the biodegradation of a hydrocarbon(s) are described below.

In one embodiment, the capability of the *Gordonia sihwensis* strain described herein to biodegrade hydrocarbons is assessed by a technique known to one of skill in the art. In a specific embodiment, the capability of the *Gordonia sihwensis* strain described herein to biodegrade hydrocarbons is assessed using a total petroleum hydrocarbon (TPH) assay, such as the TPH assay referenced in the example section herein. The TPH assay referenced in the example below provides you with the percentage of total hydrocarbons recovered; the percentage of hydrocarbons biodegraded may be obtained by subtracting the percentage of total hydrocarbons recovered from 100%.

In another aspect, the *Gordonia sihwensis* strain described herein sequesters hydrocarbons and biodegrades hydrocarbons. In one embodiment, a method for sequestering and biodegrading hydrocarbons comprises contacting a hydrocarbon composition with a culture or an inoculum of the *Gordonia sihwensis* strain described herein under conditions which permit the sequestration and biodegradation of the hydrocarbon(s) present in the composition. In another embodiment, a method for sequestering and biodegrading hydrocarbons comprises contacting a hydrocarbon composition with a composition of the *Gordonia sihwensis* strain described herein under conditions which permit the sequestration and biodegradation of the hydrocarbon(s) present in the composition. In a specific embodiment, the bacterial composition is a biologically pure culture of the *Gordonia sihwensis* strain described herein. Non-limiting examples of conditions which permit the sequestration and biodegradation of a hydrocarbon(s) are described below.

In certain embodiments, an inoculum of the *Gordonia sihwensis* strain described herein is contacted with a hydrocarbon composition in a vessel, tank or other suitable container (e.g., a bioreactor). In other embodiments, a hydrocarbon composition is contacted with a composition comprising a culture of the *Gordonia sihwensis* strain described herein in a vessel, tank (e.g., slurrification tank) or other suitable container (e.g., a bioreactor or flask) after the bacteria have been permitted to proliferate. In a specific embodiment, a hydrocarbon composition is contacted with a composition comprising a biologically pure culture of the *Gordonia sihwensis* strain described herein in a vessel, tank (e.g., slurrification tank) or other suitable container (e.g., a bioreactor or flask). In another embodiment, a hydrocarbon composition is contacted with a composition comprising the *Gordonia sihwensis* strain described herein and one or more other microorganisms (e.g., bacterial species) in a vessel, tank (e.g., slurrification tank) or other suitable container (e.g., a bioreactor or flask). In certain embodiments, the one or more other microorganisms are capable of sequestering and/or biodegrading oil.

In certain embodiments, a hydrocarbon composition is contacted with a composition comprising the *Gordonia sihwensis* strain described herein in a vessel, tank (e.g., slurrification tank) or other suitable container (e.g., bioreactor or flask) after the bacteria have entered the log phase in their growth (e.g., approximately 6 hours to approximately 18 hours, approximately 8 hours to approximately 16 hours, approximately 10 hours to approximately 18 hours, or approximately 12 hours to approximately 18 hours after inoculating the bacteria into the culture medium). In specific embodiments, a hydrocarbon composition is contacted with a composition comprising a biologically pure culture of the *Gordonia sihwensis* strain described herein in log phase growth in a vessel, tank (e.g., slurrification tank) or other suitable container (e.g., bioreactor or flask). In some embodiments, a hydrocarbon composition is contacted with a composition comprising the *Gordonia sihwensis* strain described herein in log phase growth and one or more other microorganisms (e.g., bacterial species) in a vessel, tank (e.g., slurrification tank) or other suitable container (e.g., bioreactor or flask). In certain embodiments, the one or more other microorganisms are capable of sequestering and/or biodegrading oil.

In certain embodiments, a hydrocarbon composition is contacted with a composition comprising the *Gordonia sihwensis* strain described herein in a vessel, tank (e.g., slurrification tank) or other suitable container (e.g., a bioreactor or flask) after the bacteria have entered the stationary phase in their growth (e.g., approximately 18 hours to approximately 22 hours or approximately 18 hours to approximately 24 hours after inoculating the bacteria into the culture medium). In specific embodiments, a hydrocarbon composition is contacted with a composition comprising a biologically pure culture of the *Gordonia sihwensis* strain described herein in the stationary phase of growth in a vessel, tank (e.g., slurrification tank) or other suitable container (e.g., a bioreactor or flask). In some embodiments, a hydrocarbon composition is contacted with a composition comprising the *Gordonia sihwensis* strain described herein in the stationary phase of growth and one or more other microorganisms (e.g., bacterial species) in a vessel, tank (e.g., slurrification tank) or other suitable container (e.g., a bioreactor or flask). In certain embodiments, the one or more other microorganisms are capable of sequestering and/or biodegrading oil.

In some embodiments, a hydrocarbon composition is contacted with a composition comprising a suitable microbial culture medium and the *Gordonia sihwensis* strain described herein in a vessel, tank (e.g., slurrification tank) or other suitable container (e.g., a bioreactor or flask) after the bacteria have been permitted to proliferate. In a specific embodiment, a hydrocarbon composition is contacted with a composition comprising a suitable microbial culture medium and the *Gordonia sihwensis* strain described herein in a vessel, tank (e.g., slurrification tank) or other suitable container (e.g., bioreactor or flask) after the bacteria have entered the log phase in their growth (e.g., approximately 6 hours to approximately 18 hours, approximately 8 hours to approximately 16 hours, approximately 10 hours to approximately 18 hours, or approximately 12 hours to approximately 18 hours after inoculating the bacteria into the culture medium). In another specific embodiment, a hydrocarbon composition is contacted with a composition comprising a suitable microbial culture medium and the *Gordonia sihwensis* strain described herein in a vessel, tank (e.g., slurrification tank) or other suitable container (e.g., a bioreactor or flask) after the bacteria have entered the stationary phase in their growth (e.g., approximately 18 hours to approximately 22 hours or approximately 18 hours to approximately 24 hours after inoculating the bacteria into the culture medium).

The vessel, tank or container in which the bacterial composition and the hydrocarbon composition are combined can be any vessel, tank or container commonly used to culture microorganisms, such as flasks or bioreactors, including by way of example and not limitation, stirred-tank or airlift bioreactors (suspension reactors). In certain embodiments, the vessel or container is a 5 mL, 10 mL, 20 mL, 50 mL, 100 mL, 200 mL, 500 mL, 1 L, 2 L, 3, L, 4 L, 5 L, 10 L, 100 L, 500 L, 1000 L, 5000 L, 10000 L, or 15000 L vessel, tank or container commonly used to culture microorganisms. The vessel or container may be suitable for laboratory use or commercial use.

In some embodiments, a hydrocarbon composition and a composition comprising the *Gordonia sihwensis* strain described herein are mixed in a slurrification tank and then transferred to a bioreactor. In certain embodiments, a hydrocarbon composition and a composition comprising the *Gordonia sihwensis* strain described herein are mixed in a slurrification tank for approximately 30 minutes to approximately 10 hours, approximately 30 minutes to approximately 5 hours, or approximately 30 minutes to approximately 3 hours and then transferred to a bioreactor.

Any device used in the art for maintaining culture conditions (such as temperature, pH, oxygenation, etc.) may be used as part of, or in conjunction with, a vessel, tank or container commonly used to culture microorganisms. In a specific embodiment, the temperature of the bacterial/hydrocarbon composition mixture is maintained at approximately 25° C. to approximately 45° C., approximately 30° C. to approximately 45° C., approximately 35° C. to approximately 45° C., approximately 35° C. to approximately 40° C. In another embodiment, the temperature of the bacterial/hydrocarbon composition mixture is maintained at approximately 30° C., 31° C., 32° C., 33° C., 34° C., 35° C., 36° C., 37° C., 38° C., 39° C., 40° C., 41° C., 42° C., 43° C., 44° C., or 45° C. In certain embodiments, the pH of the bacterial/ hydrocarbon composition mixture is maintained at approximately pH 6.0 to approximately pH 8.0, approximately pH 6.8 to approximately pH 7.6, approximately pH 7.0 to approximately pH 7.6, approximately pH 7.0 to approximately pH 7.4, approximately pH 7.0 to approximately pH 7.2 or approximately pH 7.0. In another embodiment, the bacterial/hydrocarbon composition is shaken at approximately 10 rpm to approximately 25 rpm, approximately 25 to approximately 50 rpm, approximately 25 to approximately 75 rpm, approximately 50 to approximately 100 rpm, or approximately 75 rpm to approximately 100 rpm. In another embodiment, the bacterial/hydrocarbon composition mixture is shaken at approximately 100 rpm to approximately 400 rpm or approximately 150 rpm to approximately 300 rpm in the vessel or container. In a specific embodiment, the bacterial/hydrocarbon composition mixture is shaken at approximately 150 rpm or 300 rpm. In another embodiment, sufficient aeration is provided to maintain a sufficient concentration of dissolved oxygen in the vessel or container. In a specific embodiment, sufficient aeration is provided to maintain a dissolved oxygen concentration of approximately 0.5 mg/L to approximately 25 mg/L, approximately 1 mg/L to approximately 25 mg/L, approximately 1 mg/L to approximately 20 mg/L, approximately 1 mg/L to approximately 15 mg/L, approximately 1 mg/L to approximately 10 mg/L, approximately 1 mg/L to approximately 5 mg/L, or approximately 5 mg/L to approximately 20 mg/L.

5.3 Hydrocarbon Compositions

As used herein, the term "hydrocarbon composition" refers to a composition comprising a quantity of at least one hydrocarbon. In a specific embodiment, a hydrocarbon composition comprises one, two, three or more hydrocarbons. In another embodiment, a hydrocarbon composition comprises only one type of hydrocarbon. In another embodiment, a hydrocarbon composition comprises two or more types of hydrocarbons. In another embodiment, a hydrocarbon composition comprises a mixture or combination of different types of hydrocarbons.

In certain embodiments, approximately 0.5% to approximately 65%, approximately 1% to approximately 65%, approximately 5% to approximately 65%, approximately 10% to approximately 65%, approximately 25% to approximately 65% or approximately 30% to approximately 65% of a hydrocarbon composition is composed of one or more hydrocarbons. In some embodiments, approximately 5% to approximately 30%, approximately 10% to approximately 30%, approximately 15% to approximately 30%, approximately 20% to approximately 30%, or approximately 25% to approximately 30% of a hydrocarbon composition is composed of one or more hydrocarbons. In other embodiments, approximately 5% to approximately 30%, approximately 0.5% to approximately 15%, approximately 0.5% to approximately 10%, approximately 0.5% to approximately 5%, or approximately 0.5% to approximately 2% of a hydrocarbon composition is composed of one or more hydrocarbons.

In certain embodiments, a particular hydrocarbon accounts for approximately 0.5% to approximately 95%, approximately 10% to approximately 95%, approximately 25% to approximately 95%, approximately 50% to approximately 95%, or approximately 75% to approximately 95% of the total hydrocarbon content in a hydrocarbon composition. In some embodiments, a particular hydrocarbon accounts for approximately 10% to approximately 75%, approximately 10% to approximately 50%, approximately 10% to approximately 25%, approximately 25% to approximately 50%, or approximately 50% to approximately 75% of the total hydrocarbon content in a hydrocarbon composition.

In certain embodiments, a hydrocarbon composition comprises two or more types of hydrocarbons with each hydrocarbon accounting for a certain percentage of the total hydrocarbon content of the composition. In some embodiments, a first type of hydrocarbon accounts for approximately 0.5% to approximately 15% of the total hydrocarbon content of a hydrocarbon composition and a second type of hydrocarbon accounts for approximately 85% to approximately 95% of the total hydrocarbon content in a hydrocarbon composition. In other embodiments, a first type of hydrocarbon accounts for approximately 10% to approximately 40% of the total hydrocarbon content of a hydrocarbon composition and a second type of hydrocarbon accounts for approximately 60% to 90% of the total hydrocarbon content of a hydrocarbon composition. In other embodiments, a first type of hydrocarbon accounts for approximately 25% to approximately 60% of the total hydrocarbon content of a hydrocarbon composition and a second type of hydrocarbon accounts for approximately 40% to approximately 75% of the total hydrocarbon content of a hydrocarbon composition.

Hydrocarbons include, but are not limited to, aliphatic hydrocarbons, aromatic hydrocarbons, nitro-aromatic hydrocarbons, halo-aliphatic hydrocarbons and halo-aromatic hydrocarbons. Non-limiting examples of hydrocarbons include alkanes (e.g., methane, ethane, propane, butane, isobutane, pentane, isopentane, neopentane, hexane, octane, nonane, and decane), alkenes (e.g., ethene, propene, butene, pentene, hexane, heptene, octane, nonene, and decene), alkynes (e.g., ethyne, propyne, butyne, pentyne, hexyne, heptyne, octyne, nonyne, and decyne), cycloalkanes (e.g., cyclopropane, cyclobutane, methylcyclopropane, cyclopentane, cyclohexane, cycloheptane, methylcyclohexane, cyclooctane, cyclononane and cyclodecane), alkadienes (e.g., allene, butadiene, pentadiene, isoprene, hexadiene, heptadiene, octadiene, nonadiene, and decadiene), and aromatic hydrocarbons (e.g., benzene, naphthalene, anthracene, toluene, xylenes, ethylbenzene, methylnaphthalene, aniline, phenol, and dimethylphenol).

In a specific embodiment, a hydrocarbon composition comprises one, two or more, or a combination of a C10 to C20 n-alkane, a C10 to C20 n-alkene, and an isoalkane. In another embodiment, a hydrocarbon composition comprises one, two or more of the following: decane, undecane, dodecane, tridecane, tetradecane, pentadecane, and hexadecane, heptadecane, octadecane, nonadecane and eicosane. In another embodiment, a hydrocarbon composition comprises one, two or more of the following: isobutene, 2,4-dimethylpentane, isooctane, and 2,2,4-trimethyldecane. In another embodiment, a hydrocarbon composition comprises a paraffin. In another embodiment, a hydrocarbon composition comprises an isoparaffin. In another embodiment, a hydrocarbon composition comprises a cycloparaffin. In certain embodiments, a hydrocarbon composition comprises a mixture of isoparaffins, n-paraffins, and cycloparaffins. In some embodiments, a hydrocarbon composition comprises a mixture of isoparaffins, n-paraffins, cycloparaffins and aromatics.

In a specific embodiment, a hydrocarbon composition comprises a base oil. Base oils include, but are not limited to, synthetic base oils, mineral base oils and diesel. Non-limiting examples of synthetic base oils include Estegreen (Chevron), Ecoflow (Chevron), Saraline (Shell MDS), Mosspar H (PetroSA), Sarapar (Shell MDS), Baroid Alkane (Halliburton), XP-07 (Halliburton), Inteq (Baker Hughes Drilling Fluids), Novadrill (M-I Swaco), Biobase (Shrieve Chemicals), Sasol C1316 paraffin (Sasol), Isoteq (Baker Hughes Drilling Fluids), Amodrill (BP Chemicals), Petrofree Ester (Halliburton), Finagreen Ester (Fina Oil and Chemical), CPChem internal olefins (ChevronPhillips Chemical), and Neoflo olefins (Shell Chemicals). Non-limiting examples of mineral oils include Escaid (Exxon), Vassa LP (Vassa), EDC-95-11 (Total), EDC99-DW (Total), HDF-2000 (Total), Mentor (Exxon), LVT (ConocoPhillips), HDF (Total), BP 83HF (BP), DMF 120HF (Fina), DF-1 (Total), EMO 4000, Shellsol DMA (Shell), IPAR 35 LV (PetroCanada), IPAR 35 (PetroCanada), Telura 401 (Exxon), SIPDRILL (SIP Ltd.), Puredrill® IA35LV, white oil (Ametek; Paoli, Pa.), and Clairsol (Carless Solvents). Other examples of base oils include, but are not limited to, crude oil, diesel oil. Ametek® (Ametek; Paoli, Pa.). Isomerized Alpha Olefin $C_{16}$ (Chevron Phillips Chemical Company), Isomerized Alpha Olefin $C_{18}$ (Chevron Phillips Chemical Company), Isomerized Alpha Olefin $C_{16-18}$ (65:35) (Chevron Phillips Chemical Company), and kerosene.

In some embodiments, a hydrocarbon composition does not contain a surfactant. In other embodiments, a hydrocarbon composition comprises a surfactant. As used herein, the term "surfactant" refers to organic substances having amphipathic structures (namely, they are composed of groups of opposing solubility tendencies, typically an oil-soluble hydrocarbon chain and a water-soluble ionic group) which have the property of adsorbing onto the surfaces or interfaces of a system and of altering to a marked degree the surface or interfacial free energies of those surfaces (or interfaces) As used in the foregoing definition of surfactant, the term "interface" indicates a boundary between any two immiscible phases and the term "surface" denotes an interface where one phase is a gas, usually air. Surfactants can be classified, depending on the charge of the surface-active moiety, into anionic, cationic, and nonionic surfactants. Surfactants are often used as wetting, emulsifying, solubilizing, and dispersing agents. Non-limiting examples of surfactants include fatty acids, soaps of fatty acids, fatty acid derivates, lecithin, crude tall oil, oxidized crude tall oil, organic phosphate esters, modified imidazolines, modified amidoamines, alkyl aromatic sulfates, alkyl aromatic sulfonates, organic esters, and polyhydric alcohols. Other examples of surfactants include amido-amines, polyamides, polyamines, esters (such as sorbitan, monooleate polyethoxylate, and sorbitan dioleate polyethoxylate), imidazolines, and alcohols.

In certain embodiments, a hydrocarbon composition does not contain $CaCl_2$. In other embodiments, a hydrocarbon composition comprises $CaCl_2$.

In a specific embodiment, a hydrocarbon composition comprises a drilling fluid. In one embodiment, the drilling fluid is a water based drilling fluid. In another embodiment, the drilling fluid is a non-aqueous drilling fluid. Non-limiting examples of drilling fluids include Aqua-Drill™ (Baker Hughes), Plus System (Baker Hughes), Aqua-Drill™ System (Baker Hughes), Bio-Lose 90 System v, Carbo-Core System (Baker Hughes), Carbo-Drill® System (Baker Hughes), Clear-Drill® DIF System (Baker Hughes), Deep Water Fluid System (Baker Hughes), Max-Bridge$^{SM}$ System (Baker Hughes), Micro-Primes$^{SM}$ System (Baker Hughes), New-Drill® System (Baker Hughes). OMNIFLOW® DIF System (Baker Hughes), PERFFLOW® 100 DIF System (Baker Hughes), PERFFLOW® DIF System (Baker Hughes), PERFFLOW® HD DIF System (Baker Hughes), PERFFLOW® System (Baker Hughes), PERFORMAX$^{SM}$ System (Baker Hughes), PYRO-Drill® System (Baker Hughes), RHEO-Logic$^{SM}$ System (Baker Hughes), SCIFLOW™ DIF System (Baker Hughes), SYN-TEQ® System (Baker Hughes), and TERRA-MAX$^{SM}$ System (Baker Hughes). In a specific embodiment, the drilling fluid is a synthetic or mineral-based drilling fluid. Examples of synthetic and mineral-based drilling fluids include, but are not limited to, Petrofree (Halliburton), Petrofree LV (Halliburton), Petrofree SF (Halliburton), Coredril-N (Halliburton), Encore (Halliburton), Integrade (Halliburton), Innovert (Halliburton), Accolade (Halliburton), Versadril (M-I Swaco), Versaclean (M-I Swaco), Paraland (M-I Swaco), Ecogreen (M-I Swaco), Trudrill (M-I Swaco), Novapro (M-I Swaco), Novatec (M-I Swaco), Trucore (M-I Swaco), Parapro (M-I Swaco), Versapro (M-I Swaco), Versapro LS (M-I Swaco), Rheliant (M-I Swaco), Magma-Drill (Baker Hughes), Magma-Teq (Baker Hughes), Syn-Core (Baker Hughes), Optidrill (Newpark), Optiphase (Newpark), Cyberdrill (Newpark), Cyberphase (Newpark), Confi-Drill (SCOMI), Confi-Dense (SCOMI), Extra-Vert (SCOMI), Opta-Vert (SCOMI), and Opta-Vert 100 (SCOMI).

In a specific embodiment, a hydrocarbon composition comprises drill cuttings. In another specific embodiment, a hydrocarbon composition comprises or is a petroleum product, such as oil, gasoline or diesel. In another embodiment, a hydrocarbon composition comprises water contaminated with one or more hydrocarbons, such as oil, gasoline or diesel. In another embodiment, a hydrocarbon composition comprises soil or sludge contaminated with one or more hydrocarbons.

5.4 Storage of Bacteria

The *Gordonia sihwensis* strain described herein may be stored under any conditions that preserve the viability of the strain. Techniques for storing bacteria are well-known to one of skill in the art. In one embodiment, the *Gordonia sihwensis* strain described herein is frozen in Brucella/glycerol and stored at approximately −70° C. to approximately −80° C. or in a liquid nitrogen tank. The strain may be thawed, streaked onto a trypticase soy agar (TSA) or a TSA sheep's blood agar plate, or a TSA/Estegreen base oil agar plate and incubated at about 35° C. prior to use. In a specific embodiment, the strain is sub-cultured every 3 to 10 days to prevent overgrowth on the agar plates.

5.5 Kits

In one aspect, described herein is a kit comprising, in a container (e.g., a vial or plate), the *Gordonia sihwensis* strain described herein. In a specific embodiment, described herein is a kit comprising, in a container (e.g., a vial or plate), a biologically pure culture of the *Gordonia sihwensis* strain described herein. In another embodiment, provided herein is a kit comprising, in one or more containers, the *Gordonia sihwensis* strain described herein and one or more other microorganisms (e.g., one or more bacterial species). In certain embodiments, the one or more other microorganisms is capable of sequestering and/or biodegrading oil. In specific embodiments, the kit further comprises instructions for use of the *Gordonia sihwensis* strain described herein. For example, in certain embodiments, the kit includes instructions for growing the bacteria, sequestering hydrocarbons and/or biodegrading hydrocarbons.

6. EXAMPLE 6.1 *Gordonia Sihwensis* Strain

The *Gordonia sihwensis* strain deposited with the ATCC was isolated from a biopile in Texas. The bacterial strain is a gram-positive, rod-shaped organism from the species *Gordonia sihwensis*. The ribotyping results for the deposited strain are shown in FIG. 1.

6.2 Growth Characteristics of the Bacteria

Approximately two loopfuls of the *Gordonia sihwensis* strain described herein (which is approximately 20,000 CFU to approximately 5,000,000 CFU) was inoculated into flasks containing 50 mL of 100% tryptic soy broth (TSB) fermentation media (EMD Chemicals; Gibbstown, N.J.) The flasks were shaken at 35° C. at 150 rpm. Aliquots of 1 mL were taken at approximately 0, 2, 4, 6, 8, 10, 12, 14, 16, 18, 20 22, and 24 hours after inoculation and spectrophotometry readings at 590 nm were performed. In addition, aliquots of 1 mL were taken at each time point (i.e., 0, 2, 4, 6, 8, 10, 12, 14 16, 18, 20, 22 and 24 hours after inoculation of the TSB), diluted in sterilized deionized water to various concentrations and plated onto tryptic soy agar (TSA). The TSA plates were incubated at 35° C. for 24 hours and colony forming units (CFU) were counted. As shown in FIG. 2, the bacteria entered log phase between about 8 and 14 hours and after a brief stationary phase between about 14 and 18 hours, entered a second log phase between about 18 and 22 hours. At about 22 hours, the CFU decreased indicating that the viability of the bacteria had decreased.

6.2 Sac-Like Structure Formation

The *Gordonia sihwensis* strain described herein forms a sac-like structure in growth media when base oil is added to the media-bacteria. Approximately two loopfuls of the *Gordonia sihwensis* strain described herein (which is approximately 20,000 CFU to approximately 5,000,000 CFU) was inoculated into a flask containing 50 mL of TSB and the flask was incubated at 35° C. at 150 rpm. After approximately 22 hours, 1 mL of base oil (2 vol. % of Estegreen (Chevron) in microbial culture medium) and 0.02 mL of Oil Red O (EMD Chemicals; Gibbstown, N.J.), an oil soluble dye, were added to the flask and the flask was shaken at 35° C. at 150 rpm. The oil soluble dye was added to the flask to visually observe the base oil added to the flask. The dye is red in the presence of oil. Approximately 0 minutes, 2 minutes, 5 minutes, 13 minutes, 30 minutes, 1 hour and 2 hours after the addition of the base oil and oil soluble dye, aliquots of the bacteria were taken from the flask and photos of the bacteria at 40× magnitude under the microscope were taken (see FIGS. 3A-3G). At approximately 0 minutes, free and clumped bacteria are observed, and the oil soluble dye is clearly visible. As shown in FIG. 3B, approximately 2 minutes after the addition of the base oil and oil soluble dye to the flask, sac-like structures begin to form and oil soluble dye becomes less visible. As time lapses, the sac-like structures become more structured and the oil soluble dye becomes less visible. By approximately 5 minutes after the addition of the base oil and oil soluble dye to the flask, the sac-like structures are well formed (FIG. 3C). Approximately 30 minutes after the addition of the base oil and oil soluble dye, an extensive network of stretched and collapsed sac-like structures are observed (FIG. 3E). Without being bound by any theory, it is believed that the sac-like structures form when the base oil is added to the flask to gather and trap the oil.

6.3 Effect of Growth Conditions on Formation of Sac-Like Structures

Effect of Shaking on Formation of Sac-Like Structures

The effect of shaking at 150 rpm after the addition of base oil (2 vol. % base oil in microbial culture medium) and shaking at 300 rpm after the addition of base oil (2 vol. % of Estegreen (Chevron) in microbial culture medium) on the formation of sac-like structures was compared. Approximately two loopfuls of the *Gordonia sihwensis* strain described herein (which is approximately 20,000 CFU to approximately 5,000,000 CFU) was inoculated into two flasks, each flask containing 50 mL of 100% TSB, and each flask was incubated at 35° C. at 150 rpm. After approximately 20 hours, 1 mL of base oil (2 vol. % of Estegreen (Chevron) in microbial culture medium) and 0.02 mL of Oil Red O (EMD Chemicals; Gibbstown, N.J.) were added to each flask. One flask was shaken at 35° C. at 150 rpm and the other flask was shaken at 35° C. at 300 rpm. After certain periods of time, aliquots were taken from each flask and the formation of the sac-like structures and visibility of the oil soluble dye was observed using a microscope. Although the sac-like structures formed more quickly in the flask shaken at 300 rpm, there was no noticeable difference between the flask shaken at 150 rpm and the flask shaken at 300 rpm after 10 minutes.

The effect of shaking at 150 rpm while growing the bacteria overnight before the addition of base oil (2 vol. % of Estegreen (Chevron) in microbial culture medium) was compared to the effect of shaking at 300 rpm while growing the bacteria overnight before the addition of base oil (2 vol. % of Estegreen (Chevron) in microbial culture medium) on the formation of sac-like structures was compared. Approximately two loopfuls of the *Gordonia sihwensis* strain described herein (which is approximately 20,000 CFU to approximately 5,000,000 CFU) was inoculated into two flasks, each flask containing 50 mL of 100% TSB. One flask was shaken at 35° C. at 150 rpm and the other flask was shaken at 35° C. at 300 rpm. After approximately 20.5 hours, 1 mL of base oil (2 vol. % of Estegreen (Chevron) in microbial culture medium) was added to each flask and the flasks were incubated at 35° C. at 300 rpm. After approximately 15 minutes, an aliquot was taken from each flask and the formation of the sac-like structures and visibility of the oil soluble dye was observed using a microscope. Although the sac-like structures were slightly more agglomerated in the flask shaken at 300 rpm than the flask shaken at 150 rpm, the difference was not significant.

Effect of Media Type on Formation of Sac-Like Structures

The effect of different types of media on the formation of sac-like structures was assessed. Approximately two loopfuls of the *Gordonia sihwensis* strain described herein (which is approximately 20,000 CFU to approximately 5,000,000 CFU) was inoculated into four flasks and each flask was incubated at 35° C. at 150 rpm. One flask contained 50 mL of nutrient broth (EMD Chemicals; Gibbstown, N.J.), another flask contained 50 mL of TSB (EMD Chemicals; Gibbstown, N.J.), another flask contained 50 mL of 50/50 TSB/enhanced Inakollu mineral media (Hung and Shreve (2004), "Biosurfactant Enhancement of Microbial Degradation of Various Structural Classes of Hydrocarbon in Mixed Waste Systems", Environ. Engineering Science 21(4): 463-469; see Table 1 below for the formula of Inakollu Media and Enhanced Inakollu Media), and the fourth flask contained 50 mL of brain heart infusion (BHI) broth. After approximately 20 hours, 1 mL of base oil (2 vol. % of Estegreen (Chevron) in microbial culture medium) and 0.02 mL of Oil Red O (EMD Chemicals; Gibbstown, N.J.) was added to each flask and the flasks were shaken at 35° C. at 300 rpm. After approximately 15 minutes, an aliquot of 0.5 mL was taken from each flask and the formation of the sac-like structures was observed using a microscope. Sac-like structure formation was best using BHI followed by TSB, then 50/50 TSB/enhanced Inakollu mineral media, and then nutrient broth.

TABLE 1

| Salt | Inakollu Media | Enhanced Inakollu Media |
| --- | --- | --- |
| $KH_2PO_4$ | 4 g/L | 4 g/L |
| $K_2HPO_4$ | 5 g/L | 5 g/L |
| $NaNO_3$ | 2 g/L | 11.2 g/L |
| NaCl | 0.5 g/L | 0.5 g/L |
| KCl | 0.5 g/L | 0.5 g/L |
| $CaCl_2$ | 0.025 g/L | 0.025 g/L |
| $FeSO_4$ | 0.25 mg/L | 1.25 mg/L |

TABLE 1-continued

| Salt | Inakollu Media | Enhanced Inakollu Media |
|---|---|---|
| $H_3BO_3$ | 0.45 mg/L | 2.25 mg/L |
| $ZnSO_4 \cdot 7H_2O$ | 0.75 mg/L | 3.75 mg/L |
| $MnSO_4 \cdot 7H_2O$ | 0.75 mg/L | 3.75 mg/L |

Effect of Temperature on Formation of Sac-Like Structures

The effect of temperature on the formation of sac-like structures was assessed. Approximately two loopfuls of the *Gordonia sihwensis* strain described herein (which is approximately 20,000 CFU to approximately 5,000,000 CFU) was inoculated into three flasks, each flask containing 50 mL of 100% TSB, and each flask was incubated at 35° C. at 150 rpm. After approximately 20.5 hours, 1 mL of base oil (2 vol. % of Estegreen (Chevron) in microbial culture medium) was added to each flask. One flask was incubated at 31° C. at 150 rpm, another flask was incubated at 35° C. at 150 rpm, and the third flask was incubated at 40° C. at 150 rpm. After approximately 15 minutes, an aliquot of 0.5 mL was taken from each flask and the formation of the sac-like structures was observed using a microscope. Sac-like structure formation after approximately 15 minutes was best at 40° C., followed by 35° C. and then 31° C.

Effect of pH on Formation of Sac-Like Structures

The effect of pH on the formation of sac-like structures was assessed. Approximately two loopfuls of the *Gordonia sihwensis* strain described herein (which is approximately 20,000 CFU to approximately 5,000,000 CFU) was inoculated into three flasks, each flask containing 50 mL of 100% TSB, pH 7 and each flask was incubated at 35° C. at 150 rpm. After approximately 20.5 hours, 1 mL of base oil (2 vol. % of Estegreen (Chevron) in microbial culture medium) was added to each flask. One flask was incubated at 35° C. at 300 rpm at pH 6 for 15 minutes, another flask was incubated at 35° C. at 300 rpm at pH 7 for 15 minutes, and the third flask was incubated at 35° C. at 300 rpm at pH 8 for 10 minutes. An aliquot of 0.5 mL was taken from each flask and the formation of the sac-like structures was observed using a microscope. Sac-like structure formation was best at pH 7, followed by pH 8 and then pH 6.

Effect of $CaCl_2$ on Formation of Sac-Like Structures

The effect of $CaCl_2$ on the formation of sac-like structures was assessed. Approximately two loopfuls of the *Gordonia sihwensis* strain described herein (which is approximately 20,000 CFU to approximately 5,000,000 CFU) was inoculated into two flasks, each flask containing 50 mL of 100% TSB, pH 7 and each flask was incubated at 35° C. at 150 rpm. After approximately 20 hours, 1 mL of base oil (2 vol. % of Estegreen (Chevron) in microbial culture medium) was added to each flask and 0.2 grams of $CaCl_2$ was added to one of the two flasks. The flasks were incubated at 35° C. at 300 rpm for 15 minutes and then an aliquot of 0.5 mL was taken from each flask and the formation of the sac-like structures was observed using a microscope. Sac-like structures were formed in both flasks.

Effect of Surfactant on Formation of Sac-Like Structures

The effect of surfactant on the formation of sac-like structures was assessed. Approximately two loopfuls of the *Gordonia sihwensis* strain described herein (which is approximately 20,000 CFU to approximately 5,000,000 CFU) was inoculated into five flasks, each flask containing 50 mL of 100% TSB, pH 7 and each flask was incubated at 35° C. at 150 rpm. After approximately 20 hours, 1 mL of base oil (2 vol. % of Estegreen (Chevron) in microbial culture medium) was added to each flask, and no surfactant was added to one flask, 0.02% Triton® X-100 (Rohm & Haas; Philadelphia, Pa.) was added to two flasks, 0.12% Centrolex® lecithin (Central Soya; Fort Wayne, N.J.) was added to another flask, and 0.6% rhamnolipid biosurfactant (Jeneil Biosurfactant; Saukville, Wis.) was added to the fifth flask. The flasks were incubated at 35° C. at 300 rpm for 15 minutes and then an aliquot of 0.5 mL was taken from each flask and the formation of the sac-like structures was observed using a microscope. As shown in FIGS. 4B-4E, the formation of sac-like structures was adversely affected by the presence of surfactant.

Effect of Drill Solids on Formation of Sac-Like Structures

The effect of drill solids on the formation of sac-like structures was assessed. Drill solids were made from drill cuttings that were extracted with solvent to remove the drilling fluid, then sieved to a uniform particle size. Approximately two loopfuls of the *Gordonia sihwensis* strain described herein (which is approximately 20,000 CFU to approximately 5,000,000 CFU) was inoculated into three flasks, each flask containing 50 mL of 100% TSB, pH 7 and each flask was incubated at 35° C. at 150 rpm. After approximately 20 hours, 1 mL of base oil (2 vol. % of Estegreen (Chevron) in microbial culture medium) was added to each flask, and no drill solids was added to one flask, 5 grams of drill solids was added to another flask, and 10 grams of drill solids was added to the third flask. The flasks were incubated at 35° C. at 300 rpm for 15 minutes and then an aliquot of 0.5 mL was taken from each flask and the formation of the sac-like structures was observed using a microscope. As shown in FIGS. 5A-5C, the sac-like structures formed in the presence of the drill solids.

Effect of Different Types of Oil on Formation of Sac-Like Structures

The effect of different types of oil on the formation of sac-like structures was assessed. Approximately two loopfuls of the *Gordonia sihwensis* strain described herein (which is approximately 20,000 CFU to approximately 5,000,000 CFU) was inoculated into six flasks, each flask containing 50 mL of 100% TSB, pH 7 and each flask was incubated at 35° C. at 150 rpm. After approximately 20 hours, 1 mL of base oil (2 vol. % Estegreen (Chevron) in microbial culture medium) was added to one flask, 1 mL of No. 2 diesel was added to another flask, 1 mL of Puredrill® IA35LV (Petro Canada; Canada) was added to another flask, 1 mL of Ametek® white oil (Ametek; Paoli, Pa.) was added to another flask, 1 mL of kerosense was added to another flask, and 1 mL of HDF-2000 (Total) was added to the sixth flask. The flasks were incubated at 35° C. at 300 rpm. An aliquot was taken from each flask after 15 minutes and after 1 hour, and the formation of the sac-like structures was observed using a microscope. As shown in FIGS. 6A-6F (15 minutes) and FIGS. 7A-7F (1 hour), the sac-like structures formed in the presence of all of the oils tested.

6.4 Biodegradation of Oil

The ability of the *Gordonia sihwensis* strain described herein to biodegrade oil was assessed using a total petroleum hydrocarbon (TPH) assay (EPA Method 8015B Non Halogenated Organics Using GC/FID, Revision 2, December 1996).

Approximately two loopfuls of the *Gordonia sihwensis* strain described herein (which is approximately 20,000 CFU to approximately 5,000,000 CFU) was inoculated into six flasks containing either 50 mL of TSB or 50 mL of nutrient broth (NB). The conditions for growing the bacteria before the addition of 1% or 2% base oil (1 or 2 vol. % of Estegreen (Chevron) in microbial culture medium, respectively) and the conditions after the addition of 1% or 2% base oil (1 or 2 vol. % of Estegreen (Chevron) in microbial culture medium) are found in Table 2 below.

TABLE 2

Conditions

| | Growth Phase | | | | | Biodegradation | | | | | | | |
|---|---|---|---|---|---|---|---|---|---|---|---|---|---|
| Flask No. | Media | RPM | Temp. (°C.) | Time (Hrs) | % Oil[1] | Shake 10 min.[2] | Shake 18 min, 150 rpm, 35° C.[3] | Drain & Add EI[4] | Cfuge & Add EI[5] | Shake 10 min. after adding EI[6] | RPM | Temp. (°C.) | Time (Hrs) |
| 1 | TSB | 150 | 35 | 20 | 2 | N[7] | Y[8] | Y | N | NA[9] | 300 | 35 | 20 |
| 2 | TSB | 150 | 35 | 20 | 2 | N | Y | N | N | NA | 300 | 35 | 20 |
| 3 | NB | 150 | 35 | 22 | 1 | NA | N | N | Y | N | 300 | 35 | 19 |
| 4 | NB | 150 | 35 | 22 | 1 | NA | N | N | Y | Y | 300 | 35 | 19 |
| 5 | NB | 150 | 35 | 22 | 1 | Y | N | Y | N | NA | 300 | 35 | 18.5 |
| 6 | NB | 150 | 35 | 22 | 1 | Y | N | N | N | NA | 300 | 35 | 17.5 |

[1]0.5 mL of base oil (1 vol % of Estegreen in microbial culture medium) or 1 mL of base oil (2 vol. % of Estegreen in microbial culture medium) was added to the flasks.
[2]Flasks were shaken by hand for 10 minutes after the addition of 0.5 mL of Estegreen (Chevron).
[3]Flasks were shaken in a shaker oven for 18 minutes at 150 rpm at 35° C. after the addition of 1 mL of Estegreen (Chevron).
[4]After the addition of 0.5 mL of Estegreen (Chevron) and shaking by hand for 10 minutes or after the addition of 1 mL of Estegreen (Chevron) and shaking in a shaker oven for 18 minutes at 35° C., the media was drained from the flask and 50 mL of enhanced Inakollu media was added to the bacteria remaining in the flask.
[5]The contents of the flask were centrifuged, the supernatant was removed to concentrate the bacteria, and 50 mL of enhanced Inakollu media was added to the flask along with 0.5 mL of Estegreen (Chevron).
[6]The flasks were shaken by hand for 10 minutes after the contents of the flask were centrifuged, the supernatant was removed to concentrate the bacteria and 50 mL of enhanced Inakollu media was added to the flask along with 0.5 mL of Estegreen (Chevron).
[7]N means that the condition was not used.
[8]Y means that the condition was utilized.
[9]NA means not applicable and that the condition does not apply.

Approximately 17.5 to 20 hours after the addition of base oil, the contents from each flask was analyzed by TPH, and the appearance of the bacteria and media was observed. The results from the TPH analysis and the appearance of the bacteria and in the flasks are provided below in Table 3. In all of the flasks except flask number 6, the percentage of oil recovered as measured by TPH was between 49% and 57.4%. In other words, 42.6% to 51% of the total hydrocarbons present in the flasks 1 to 5 were biodegraded. In flask number 6, the percentage of oil recovered as measured by TPH was 23.3%. In other words, 76.7% of the total hydrocarbons present in flask 6 were biodegraded.

TABLE 3

Results

| No. | Floating Layer | Coagulation | Size of Coagulated Balls | Media | State of Bacteria Under Microscope | Total % Recovered Oil |
|---|---|---|---|---|---|---|
| 1 | Y[1] | Y (Slightly with swirling) | Large | Sl[3] Cloudy | Bacteria agglomeration | 50.3/53.4 |
| 2 | Y | Y | Large | Sl Cloudy | Agglomeration of sacs | 55.8 |
| 3 | Y | Y | Giant mass | Sl Cloudy | Stringy agglomeration | 57.4 |
| 4 | Y | Y | Giant ball | Sl Cloudy | Swirled agglomeration | 49 |
| 5 | Y | Y | Giant ball | Sl Cloudy | Bacteria agglomeration | 52.1 |
| 6 | N[2] (Sunk) | Y | Small | Clear | Bacteria ball | 23.3 |

[1]Y means that there was a floating layer in the flask.
[2]N means that there was no floating layer in the flask.
[3]Sl means slightly.

In another assay to assess the ability of the *Gordonia sihwensis* strain described herein to biodegrade oil, approximately two loopfuls of the *Gordonia sihwensis* strain described herein (which is approximately 20,000 CFU to approximately 5,000,000 CFU) was inoculated into fifteen flasks containing either 50 mL of nutrient broth (NB) or 50 mL of nutrient broth and enhanced Inakollu media (1:1; NB/EI). The conditions for growing the bacteria before and after the addition of base oil are found in Table 4 below.

TABLE 4

| | | Growth Phase | | | | Biodegradation Phase | | | | |
|---|---|---|---|---|---|---|---|---|---|---|
| No. | Media | RPM | Temp (°C.) | % Oil | Time (Hrs) | % Oil[1] | Bacteria Conc. | RPM | Temp (°C.) | Initial Hand Shaking[2] (min) | Shaking After 1 Hr[3] (min) |
| 1 Ctrl | NB | 150 | 35 | 0 | 22 | 0.5 | 1X | 300 | 35 | 10 | 0 |
| 2 | NB | 150 | 35 | 0 | 22 | 1 | 1X | 300 | 35 | 10 | 0 |
| 3 | NB | 150 | 35 | 0.3[4] (1 pm) | 22 | 0.5 | 1X | 300 | 35 | 10 | 0 |
| 4 | NB | 150 | 35 | 0 | 17 | 0.5 | 1X | 300 | 35 | 10 | 0 |
| 5 | NB | 150 | 35 | 0 | 22 | 0.5 | 1X | 300 | 35 | 20 | 0 |
| 6 | NB | 150 | 35 | 0 | 22 | 0.5 | 1X | 300 | 35 | 0 | 20 |
| 7 | NB/EI | 150 | 35 | 0 | 22 | 0.5 | 1X | 300 | 35 | 10 (after 20 min) | 0 |
| 8 | NB | 150 | 35 | 0 | 22 | Used to produce 2X bacteria conc. - see flask No. 9 | | | | | |
| 9 | NB | 150 | 35 | 0 | 22 | 0.5 | 2X | 300 | 35 | 10 | 0 |
| 10 | NB | 150 | 35 | 0 | 22 | 0.5 | 1X | 150 | 35 | 10 | 0 |
| 11 | NB | 150 | 35 | 0 | 22 | 0.5 | 1X | 150 | 35 | 0 | 10 |
| 12 | NB | 150 | 35 | 0 | 22 | 0.5 | 1X | 150 | 35 | 20 | 0 |
| 13 | NB/EI | 150 | 35 | 0 | 22 | 0.5 | 1X | 150 | 35 | 10 (after 20 min) | 0 |
| 14 | NB | 150 | 35 | 0 | 22 | 0.5 | 1X | 300 | 35 | 10 | 10 |
| 15 | NB | 150 | 35 | 0 | 22 | 0.5 | 1X | 150 | 35 | 10 | 10 |

[1] 1 mL of base oil (0.5 vol. % Estegreen (Chevron) in microbial culture medium) or 2 mL of base oil (1 vol. % Estegreen (Chevron) in microbial culture medium) was added to the flasks.
[2] Initial hand shaking means that the flask was hand shaken immediately after the addition of the base oil for the indicated time period.
[3] Shaking after 1 Hr means that 1 hour after the addition of the base oil, the flask was hand shaken for the indicated time period.
[4] 0.15 mL of base oil (0.3 vol. % Estegreen (Chevron) in microbial culture medium) was added to the flask.

Approximately 8 hours after the addition of base oil, the contents from each flask was analyzed by TPH. Approximately 4.5 hours and 8 hours after the addition of base oil, the appearance of the bacteria and media was observed. The results from the TPH analysis and the appearance of the bacteria and media in the flasks are provided below in Table 5. In all of the flasks, the percentage of oil recovered after 8 hours as measured by TPH was between 28.8% and 51.2%. In other words, 48.8% to 71.2% of the total hydrocarbons present in the flasks were biodegraded.

TABLE 5

| | Results after 4.5 hours | | | | Results after 8 hours | | | | | |
|---|---|---|---|---|---|---|---|---|---|---|
| No | Floating Layer[1] | Coag.[2] | Size of Coagulated Ball | Media Clear[3] | Floating Layer[1] | Coag.[2] | Size of Coagulated Ball | Media Clear[3] | Microscopic State of Bacteria | Total % Recovered Oil by TPH |
| 1 | Y | N | | Y | Y | N (Slightly Stringy) | | Y | Loose sacs | 33.3 |
| 2 | Y | Y | | Y | N (Sunk) | Y | Small | Y | Bacteria ball | 45.8 |
| 3 | Y | N | Low bacteria amount | Y | Y | N (Smooth) | | Y | Sac material | 51.2 |
| 4 | Y | Y | Low bacteria amount | Y | N (Sunk) | Y (Low amount) | Small | Y | Bacteria ball | 34.3 |
| 5 | Y | Y | | Y | N (almost all sunk) | Y (High amount) | Small | Y | Bacteria ball | 35.6 |
| 6 | Y | N (Very Stringy) | | Y | Y | Y | Average | Y | Sac/bacteria agglomeration | 47.8 |
| 7 | Y | Y | | N (Slightly Cloudy) | N < 10% floating | Y | Average | Y | Sac/bacteria agglomeration & ball | 41 |
| 8 | Y (sunk layer) | Y | | Y | N (Sunk) | Y (Smooth) | Small | Y | Bacteria ball | 38.7 |
| 9 | Y | Y | | N (Slightly Cloudy) | N < 5% floating | Y | Large | N (Sl Cloudy) | Large bacteria ball | 28.8 |
| 10 | Y | N (Slight Stringy) | | N (Slightly Cloudy) | Y | Y (mostly floating) | Average | N (Sl Cloudy) | Bacteria ball | 40.3 |

TABLE 5-continued

Results

| | Results after 4.5 hours | | | | Results after 8 hours | | | | |
| --- | --- | --- | --- | --- | --- | --- | --- | --- | --- |
| No | Floating Layer[1] | Coag.[2] | Size of Coagulated Ball | Media Clear[3] | Floating Layer[1] | Coag.[2] | Size of Coagulated Ball | Media Clear[3] | Microscopic State of Bacteria | Total % Recovered Oil by TPH |
| 11 | Y | N (Stringy) | | N (Slightly Cloudy) | N < 10% floating | Y | Large | Y | Large bacteria ball | 35.1 |
| 12 | Y | N (Slightly Stringy) | | N (Cloudy) | Y | Y | Large | N (Sl Cloudy) | Bacteria ball with liquid | 48.8 |
| 13 | Y | N (Very Stringy) | | Y | Y < 20% sinking | Y | Average | Y | Bacteria ball | 44.2 |
| 14 | Y | N (Slightly Stringy) | | N (Slightly Cloudy) | Y < 10% sinking | Y | Large | N (Sl Cloudy) | Coagulation liquid border | 49.9 |

[1]Y means that a floating layer was observed in the flask; N means that no floating layer was observed in the flask.
[2]Y means that coagulation was observed in the flask; N means that no coagulation was observed in the flask.
[3]Y means the media was clear; N means the media was not clear.

6.5 Bioreactor Test

A bioreactor yard test was performed to assess the ability of the *Gordonia sihwensis* strain described herein to biodegrade drill fluid-coated drill cuttings.

6.5.1 Material & Methods

Bioreactor Assay

Seventeen gallons of a bacterial solution containing approximately 42×10⁶ CFU/mL of the *Gordonia sihwensis* strain described herein was added to 280 gallons of nutrient broth media (AMD Chemicals) in a 10 barrel bioreactor. The *Gordonia sihwensis* strain described herein was mixed in the bioreactor with a paddle mixer stirring at 25 rpm for 24 hours at a temperature maintained between 93.8° F. and 98.4° F., a pH maintained between 7.0 and 7.6, and with a dissolved oxygen content maintained between 7.0 mg/L and 9.2 mg/L. After 24 hours, the 230 gallons of the bacteria/media mixture was pumped to a 10 barrel slurrification tank and immediately afterwards 774.6 lbs of oily cuttings were added to the slurrification tank. The 774.6 lbs of oily cuttings contained 616.61 lbs of dry cuttings and 158 lbs of Estegreen (Chevron) drilling mud. The drill cuttings were combined with the bacteria/media mixture in the tank and slurrified using a high shear centrifugal pump, a high shear agitator and a static mixer. The high shear centrifugal pump consisted of a 6×5×14 SPD 2.5 Mud Hog centrifugal pump complete with mechanical seal and a high shear impeller, driven by a 75 HP 460 V 60 Hz 1750 rpm explosion proof motor. The pump was run at full speed throughout the slurrification. The high speed agitator consisted of a 10 HP 460 V 60 Hz explosion proof mixer complete with high shear chopping impeller. The agitator was run at 100% of full speed during slurrification. The static shear mixer was 24" length×4" diameter, with 1" steel rods with 45° offset and discharge.

After 2.5 hours, the slurry was pumped to the bioreactor where it was gently mixed with a paddle mixer at 25 rpm and recirculated with a size 60 Open Throat Auger PC pump driven by a 10 HP 460 V 60 Hz mechanical variable speed drive, operating at 10% to 25% of full speed. The maximum airflow was 55 cfu/min at 6 psi. The airflow varied depending on how many air diffusers were in operation. The slurry was recirculated back through the bioreactor using a positive displacement pump to prevent settling. The bioreactor was heated with heating tape and insulating jacket. The temperature was maintained between 95° F. and 101° F., the pH was maintained between 7.0 and 7.6, and the dissolved oxygen varied between 3.0 mg/L and 9.0 mg/L in the bioreactor, 5 kg of nutrient broth powder was added during the yard test to maintain nutrient concentrations. The fluid level remained fairly constant during the yard test because there was little evaporation, although water was added occasionally through acid additions.

See FIG. 8 for a schematic of the bioreactor and slurrification tank system. As would be appreciated by those of skill in the art, the bioreactor system may further comprise any additional components (such as lines, valves, gaskets, input conduits, output conduit, recycle loops, couplings for pH and oxygen sensors and/or for NaOH and NPK injections, etc.) needed and/or desired to optimize sequestration and/or biodegradation of hydrocarbons by the deposited bacteria, and/or to enhance the effectiveness, efficiency, speed, and/or other desirable properties achievable through use of the system. It should be noted that the system depicted in FIG. 8 is in no way intended to be limiting. The controller used can be any controller that is suitable for controlling, coordinating, manipulating, and/or optimizing the operation of one or more components of the system (such as, for example, the slurrification tank and/or the bioreactor) in a manner such that the deposited bacteria sequesters and/or biodegrades hydrocarbons. In some embodiments, the controller is a semi-automatic controller that allows that any desired degree of user input and/or control during the operation of the system. In some embodiments, the controller is an automatic controller.

The bacterial count, pH, temperature, air flow rate, recirculation pump speed, degree of foaming, agitator speed, and dissolved oxygen were monitored during the yard test. The biodegradation of drill fluid-coated drilling cuttings was analyzed by TPH. Samples were taken for TPH analysis at various times during the yard test.

Preparation of Drill Cuttings

Three large (20.5" diameter×36– length) Pierre 1 shale cores (purchased from Terratek in Utah) were broken into pieces. The Pierre 1 shale has the properties listed in Table 6.

TABLE 6

| Measurement | Value |
| --- | --- |
| Bulk Density | 2.34 g/cc |
| Grain Density | 2.7 g/cc |
| Porosity | 15.8% |

TABLE 6-continued

| Measurement | Value |
| --- | --- |
| Gas Permeability | $10^{-9}$ md |
| UCS | 1600 psi |
| Confined Strength (psi) | 2,500 @ 700 |
| UC Young's Modulus | 130,000 psi |
| Poisson's Ratio | 0.36 |

The Pierre 1 shale cores were crushed into simulated cuttings. Enough shale was crushed to obtain approximately 4 drums (220 gallons) of dry cuttings.

To simulate the crushing process, pieces of Pierre 1 shale were broken into cuttings-size pieces having the particle size distribution provided in Table 7.

TABLE 7

| Size (inches) | % by weight |
| --- | --- |
| >0.75 | 2.2 |
| 0.75-0.375 | 40.5 |
| 0.375-0.15 | 34.7 |
| 0.15-0.132 | 11.1 |
| <0.132 (fines) | 11.5 |

Preparation of Chloride-Free Drilling Fluid Formulation

Approximately 2 drums of Estegreen-based drilling fluid formulation was prepared. To avoid toxicity to microorganisms, chlorides in the internal phase were eliminated by replacing calcium chloride with potassium formate. A chloride-free Estegreen-based formulation using potassium formate (HCOOK) is shown in the Table 8.

TABLE 8

| Component | Quantity |
| --- | --- |
| Estegreen | 0.724 bbl |
| Carbo-Gel | 6 lbs/bbl |
| Omni-Mul | 8 lbs/bbl |
| 30% HCOOK Brine | 0.187 bbl |
| Properties | Value |
| Density | 8.34 lbs/gal |
| Oil/Brine Ratio | 80/20 |
| Water Phase Salinity (WPS), % HCOOK | 30.0 |
| Water Activity (Aw) | 0.80 |

Preparation of Drill Cuttings Coated With Estegreen-Based Drilling Fluid 616.6 lbs of dry drill cuttings were mixed with 18.95 gallons of Estegreen-based drilling fluid utilizing a 9 cuft capacity Stow cement mixer with a 1.5 HP electric motor. The drill cuttings and drilling fluid were mixed for approximately 30 minutes before being added to the slurrification tank.

6.5.2 Results

The TPH results for the bioreactor yard test are shown in Table 9 below and FIG. 9.

TABLE 9

| Time (days) | TPH | Percent (%) of Original Recovered |
| --- | --- | --- |
| 0 | 29,702 | 100 |
| 0.08 | 22,900 | 77.1 |
| 0.09 | 17,400 | 58.6 |
| 0.25 | 18,700 | 63 |
| 0.506 | 15,900 | 53.5 |
| 0.67 | 14,500 | 48.8 |
| 0.83 | 18,600 | 62.6 |
| 1.14 | 16,700 | 56.2 |
| 1.32 | 13,100 | 44.1 |
| 1.52 | 22,200 | 74.7 |
| 1.69 | 12,500 | 42.1 |
| 1.82 | 19,000 | 64 |
| 2.13 | 16,400 | 55.2 |
| 2.29 | 14,800 | 49.8 |
| 2.45 | 14,400 | 48.5 |
| 2.76 | 11,600 | 39.1 |

The present invention is not to be limited in scope by the specific embodiments described herein. Indeed, various modifications of the invention and their equivalents, in addition to those described herein will become apparent to those skilled in the art from the foregoing description and accompanying figures. Such modifications are intended to fall within the scope of the appended claims.

Various patents, patent applications, and publications are cited herein, the disclosures of which are incorporated by reference in their entirety and for all purposes.

What is claimed is:

1. An isolated *Gordonia sihwensis* strain assigned ATCC Accession No. PTA-9635.

2. A biologically pure culture of a strain of *Gordonia sihwensis* having all the identifying characteristics of the strain of *Gordonia sihwensis* assigned ATCC Accession No. PTA-9635.

3. A composition comprising an amount of the *Gordonia sihwensis* strain of claim 1 that is viable and in an amount effective to biodegrade and sequester hydrocarbons.

4. The composition of claim 3 further comprising media suitable for growth of the viable *Gordonia sihwensis* strain.

5. The composition of claim 4 further comprising one or more hydrocarbons.

* * * * *